US006426415B1

(12) United States Patent
Jackson et al.

(10) Patent No.: US 6,426,415 B1
(45) Date of Patent: Jul. 30, 2002

(54) ALKOXY-SUBSTITUTED COMPOUNDS, METHODS AND COMPOSITIONS FOR INHIBITING PARP ACTIVITY

(75) Inventors: Paul F. Jackson, Bel Air; Keith M. Maclin, Baltimore; Jie Zhang, Ellicott City, all of MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/079,508

(22) Filed: May 15, 1998

Related U.S. Application Data

(63) Continuation-in-part of application No. 08/922,520, filed on Sep. 3, 1997.

(51) Int. Cl.$^7$ .............................................. C07D 237/30
(52) U.S. Cl. ...................................... 544/237; 546/137
(58) Field of Search ........................... 546/137; 544/237

(56) References Cited

U.S. PATENT DOCUMENTS

| | | | |
|---|---|---|---|
| 932,290 A | 8/1909 | Kacer et al. ................. | 514/330 |
| 1,001,325 A | 8/1911 | Ulman et al. | |
| 1,253,252 A | 1/1918 | Kardos et al. | |
| 1,880,441 A | 10/1932 | Heidenreich et al. | |
| 1,895,105 A | 1/1933 | Rath et al. | |
| 2,467,692 A | 4/1949 | Petrow et al. | |
| 2,593,798 A | 4/1952 | Robinson | |
| 2,612,503 A | 9/1952 | Ullyot | |
| 2,638,472 A | 5/1953 | Grewe | |
| 2,666,059 A | 1/1954 | Davis et al. | |
| 2,700,040 A | 1/1955 | Ullyot | |
| 2,892,841 A | 6/1959 | Rudner | |
| 2,992,220 A | 7/1961 | Irving et al. | |
| 3,247,212 A | 4/1966 | Johnson | |
| 3,291,801 A | 12/1966 | Montgomery | |

(List continued on next page.)

FOREIGN PATENT DOCUMENTS

| | | | | |
|---|---|---|---|---|
| BE | 562948 | 6/1958 | | |
| BE | 628255 | 2/1963 | | |
| BE | 628 255 | 5/1963 | | |
| CA | 1000701 | 11/1976 | | |
| CA | 1274339 | 7/1987 | | |
| CA | 1278141 | 10/1987 | | |
| CH | 463 778 | 10/1968 | | |
| CH | 601 246 | 6/1978 | ......... | C07D/217/24 |
| DE | D.R.P.282711 | 3/1915 | | |
| DE | 282711 | 3/1915 | | |
| DE | 963 184 | 5/1957 | | |
| DE | A-2111910 | 10/1971 | | |
| DE | A-2429515 | 1/1975 | | |
| DE | 26 50 226 | 5/1978 | | |
| DE | 33 32 633 A | 4/1985 | | |

(List continued on next page.)

OTHER PUBLICATIONS

Nuvole, Antonio et al, Synthesis of 1–Amino 4–Chloro–isoquinoline. Abstract & Citation, An 1979:137–644 Capius, 1978.*
Abstr Pap Am Chem Soc 206 (2) 1993 Slama et al.
Abstract 1994:425593 1994 Zailsev et al.
Aldrich Catalog #23,559–8.
Angew. Chem. 76:1, 50 1964 Baer et al.
Ann. 673:123–36 1964 Reid et al.
Ann. Chem. 688:177–88 1965 Reid et al.
Ann. N Y Acad Sci. 825:366–79 1997 Cosi et al.

(List continued on next page.)

Primary Examiner—Dwayne C. Jones
(74) Attorney, Agent, or Firm—Nixon & Vanderhye P.C.

(57) ABSTRACT

A compound of formula I:

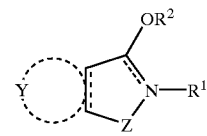

or a pharmaceutically acceptable salt, prodrug, metabolite, optical isomer or stereoisomer thereof, wherein:

$R^1$, when present, is hydrogen or lower alkyl;
$R^2$ is lower alkyl, aryl, aralkyl, lower alkanoyl, or —$(CH_2)_n$—$(CHOH)_y(CH_2)_m$A, wherein n is 1–4, y is 0 or 1, m is 0–5, and A is cycloalkyl, cycloalkenyl, lower alkanoyl, aryl, aralkyl, —$NH_2$, —NH-(lower alkyl),

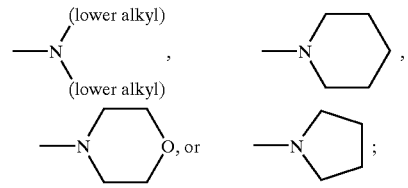

Y represents the atoms necessary to form a fused 5- to 6-membered ring that is aromatic or nonaromatic and carbocyclic or heterocyclic;
Z is
(i) —$CHR^2CHR^3$— where $R^2$ and $R^3$ are independently hydrogen, alkyl, aryl or aralkyl;
(ii) —$R^6C$=$CR^3$— where $R^6$ and $R^3$ are independently hydrogen, lower alkyl, aryl, aralkyl, chlorine, bromine or —$NR^7R^8$, where $R^7$ and $R^8$ are independently hydrogen or lower alkyl, or, $R^6$ and $R^3$, taken together, form a fused 5- to 6-membered ring that is aromatic or nonaromatic and carbocyclic or heterocyclic;
(iii) —$R^2C$=N—;
(iv) —$CR^2(OH)$—$NR^7$—; or
(v) —$C(O)$—$NR^7$—.

16 Claims, 2 Drawing Sheets

U.S. PATENT DOCUMENTS

| | | |
|---|---|---|
| 3,300,499 A | 1/1967 | Lesher et al. |
| 3,403,157 A | 9/1968 | Humber et al. |
| 3,507,872 A | 4/1970 | Hegar |
| 3,534,038 A | 10/1970 | Machatzke et al. |
| 3,557,119 A | 1/1971 | Humber et al. ............. 514/425 |
| 3,573,304 A | 3/1971 | Eberle et al. .............. 544/320 |
| 3,700,673 A | 10/1972 | Watson, Jr. ................ 544/300 |
| 3,719,684 A | 3/1973 | Unger et al. ............... 514/410 |
| 3,759,924 A | 9/1973 | Jeanmart et al. |
| 3,830,816 A | 8/1974 | Glittos et al. |
| 3,838,134 A | 9/1974 | Glauthier |
| 3,899,529 A | 8/1975 | Witzel |
| 3,900,477 A | 8/1975 | Philipp et al. |
| 3,904,671 A | 9/1975 | Minatoya |
| 3,932,643 A | 1/1976 | Gauthier |
| 3,950,343 A | 4/1976 | Philipp et al. |
| 3,978,066 A | 8/1976 | Philipp et al. |
| 3,991,064 A | 11/1976 | Brown et al. |
| 4,031,097 A | 6/1977 | Bach et al. |
| 4,082,741 A | 4/1978 | Hunger et al. |
| 4,169,897 A | 10/1979 | Meyer et al. |
| 4,218,453 A | 8/1980 | Hannart |
| 4,309,543 A | 1/1982 | Keeley |
| 4,382,943 A | 5/1983 | Winter et al. |
| RE31,617 E | 6/1984 | Beverung, Jr. et al. |
| 4,472,401 A | 9/1984 | Kennewell et al. |
| 4,594,415 A | 6/1986 | Robins et al. |
| 4,639,454 A | 1/1987 | Hesson |
| 4,740,581 A | 4/1988 | Pruett et al. ................ 514/400 |
| 4,742,171 A | 5/1988 | Martin et al. ............... 514/400 |
| 4,902,695 A | 2/1990 | Ornstein ..................... 514/400 |
| 4,902,798 A | 2/1990 | Nakamatsu et al. ........ 514/400 |
| 4,925,968 A | 5/1990 | Sestanj et al. .............. 514/400 |
| 5,032,617 A | 7/1991 | Lee et al. .................... 514/400 |
| 5,041,653 A | 8/1991 | Lee et al. .................... 514/400 |
| 5,077,035 A | 12/1991 | Wieland et al. ............. 514/400 |
| 5,177,075 A * | 1/1993 | Suto et al. ................... 514/248 |
| 5,215,738 A | 6/1993 | Lee et al. .................... 514/400 |
| 5,262,564 A | 11/1993 | Schohe et al. .............. 514/400 |
| 5,274,097 A | 12/1993 | Schohe et al. .............. 514/400 |
| 5,338,851 A | 8/1994 | Huff et al. ................... 514/400 |
| 5,391,376 A | 2/1995 | Long, Jr. et al. ........... 514/400 |
| 5,395,835 A | 3/1995 | Glase et al. ................. 514/400 |
| 5,414,001 A | 5/1995 | Ireland et al. ............... 514/400 |
| 5,420,136 A | 5/1995 | Lewis et al. ................ 514/400 |
| 5,434,188 A | 7/1995 | Boschelli et al. ........... 514/400 |
| 5,464,871 A | 11/1995 | Kun et al. ................... 514/400 |
| 5,473,074 A | 12/1995 | Kun et al. ................... 514/400 |
| 5,480,631 A | 1/1996 | De Paulis et al. |
| 5,482,975 A | 1/1996 | Kun et al. |
| 5,516,941 A | 5/1996 | Kun et al. |
| 5,587,384 A | 12/1996 | Zhang et al. |
| 5,589,483 A | 12/1996 | West ........................... 514/310 |
| 5,618,813 A | 4/1997 | Chu et al. |
| 5,633,282 A | 5/1997 | Collins et al. |
| 5,635,506 A | 6/1997 | Alberts et al. |
| 5,652,260 A | 7/1997 | Kun et al. ................... 546/300 |
| 5,652,367 A | 7/1997 | Kun et al. |
| 5,656,638 A | 8/1997 | Gaeta et al. |
| 5,659,082 A | 8/1997 | Flitter et al. |
| 5,665,710 A | 9/1997 | Rahman et al. |
| 5,670,518 A | 9/1997 | Kun et al. |
| 5,703,089 A | 12/1997 | Braña et al. |
| 5,703,116 A | 12/1997 | Gaeta et al. |
| 5,719,151 A | 2/1998 | Shall et al. |
| 5,753,674 A | 5/1998 | Kun et al. |
| 5,756,510 A | 5/1998 | Griffin et al. |
| 5,760,062 A | 6/1998 | Gaeta et al. |
| 5,767,135 A | 6/1998 | Fernandez-Pol ............ 514/300 |
| RE36,397 E | 11/1999 | Zhang et al. |
| 6,121,278 A | 9/2000 | Jackson et al. ............. 514/310 |
| 6,291,425 B1 | 9/2000 | Li et al. ...................... 514/300 |
| 6,197,785 B1 | 3/2001 | Jackson et al. ............. 544/225 |
| 6,201,020 B1 | 3/2001 | Zhang ......................... 544/310 |
| 6,235,748 B1 | 5/2001 | Li et al. ...................... 544/400 |

FOREIGN PATENT DOCUMENTS

| | | | |
|---|---|---|---|
| EP | 0 005 232 A | 11/1979 | |
| EP | 0 126 684 B1 | 11/1984 | |
| EP | 0 197 718 B1 | 10/1986 | |
| EP | 0 212 959 B1 | 3/1987 | |
| EP | 0 219 208 B1 | 4/1987 | |
| EP | 355 750 | 2/1990 | |
| EP | 0 355 750 | 2/1990 | |
| EP | 393926 | 10/1990 | |
| EP | 0 393 926 | 10/1990 | |
| EP | 0 539 805 | 5/1993 | |
| EP | 0 555 750 | 8/1993 | |
| EP | 0 638 309 A1 | 2/1995 | |
| EP | 0676 201 | 10/1995 | |
| FR | 1 199 252 | 12/1959 | |
| FR | 7 723 M | 3/1970 | |
| FR | 2 205 333 | 5/1974 | |
| FR | 2 305 182 | 10/1976 | |
| GB | 810 108 | 3/1959 | |
| GB | 810108 | 3/1959 | |
| GB | 838994 | 6/1960 | |
| GB | 1263044 | 2/1972 | |
| GB | 1379111 | 1/1975 | |
| GB | 1474775 | 5/1977 | |
| GB | 1 474 775 | 5/1977 | ......... C07D/217/24 |
| GB | 1545767 | 5/1979 | |
| JP | 4-275296 | 9/1972 | |
| JP | 3-205402 | 9/1991 | |
| JP | 032 05402 A2 | 9/1991 | |
| JP | 040 13684 A2 | 1/1992 | |
| JP | 4-275223 | 9/1992 | |
| JP | 042 75223 A2 | 9/1992 | |
| JP | 042 75296 A2 | 9/1992 | |
| JP | 4-13684 | 11/1992 | |
| WO | WO 90/07502 | 7/1990 | |
| WO | WO 92/00281 | 1/1992 | |
| WO | WO 92/05770 | 4/1992 | |
| WO | WO 92/15286 | 9/1992 | |
| WO | WO 93/05096 | 3/1993 | |
| WO | WO 93/18748 | 9/1993 | |
| WO | WO 95/04720 | 2/1995 | |
| WO | WO 95/24379 | 9/1995 | |
| WO | WO 95/29895 | 11/1995 | |
| WO | WO 95/30409 | 11/1995 | |
| WO | WO 96/28167 | 9/1996 | |
| WO | WO 96/33268 | 10/1996 | |
| WO | WO 97/30054 | 8/1997 | |
| WO | WO 97/38977 | 10/1997 | |
| WO | WO 98/27975 | 7/1998 | |
| WO | WO 99/11622 | 3/1999 | |
| WO | WO 99/11623 | 3/1999 | |
| WO | WO 99/11624 | 3/1999 | |
| WO | WO 99/11628 | 3/1999 | |
| WO | WO 99/11644 | 3/1999 | |
| WO | WO 99/11645 | 3/1999 | |
| WO | WO 99/11649 | 3/1999 | |
| WO | WO 99/59973 | 11/1999 | |
| WO | WO 99/59975 | 11/1999 | |
| WO | WO 00/39070 | 7/2000 | |
| WO | WO 00/39104 | 7/2000 | |

OTHER PUBLICATIONS

Annu. Rev. Neurosci 13, 171–82 1990 Choi et al.
Anticancer Drug Res. 7:107–17 1991 Suto et al.

Anticancer Drug Design 10(6)507–14 (Sep. 1995) Griffin et al.
Anti–Cancer Drug Design 10(6): 507–14 1995 R. Griffin et al.
Anticancer Research 11: 881–888 1991 Sakagami et al.
Arch. Pharm. Ber. Dtsch. Pharm. Ges. 300:6, 533–39 1967 Reisch.
Beilstein Handbook of Organic Chem. Reg. No. 158523 1950.
Beilstein Handbook of Organic Chem. Reg. No. 233692 1956.
Beilstein Handbook of Organic Chem. Reg. No. 618403 1988 Dokunichin.
Beilstein Handbook of Organic Chem. Reg. No. 827161 1988 Dokunichin.
Beilstein Handbook of Organic Chem. Reg. No. 821484 1988 Dokunichin.
Beilstein Handbook of Organic Chem. Reg. No. 619108 1988 Dokunichin.
Beilstein Handbook of Organic Chem. Reg. No. 657772 1988 Dokunichin.
Beilstein Handbook of Organic Chem. Reg. No. 653888 1988 Dokunichin.
Beilstein Handbook of Organic Chem. Reg. No. 807993 1988 Sielitz.
Beilstein Handbook of Organic Chem. Reg. No. 746893 1988 Dokunichin.
Beilstein Handbook of Organic Chem. Reg. No. 656117 1988 Gomes.
Beilstein Handbook of Organic Chem. Reg. No. 1571164 1988 Rokach.
Beilstein Handbook of Organic Chem. Reg. No. 1541605 1988 Humber et al.
Beilstein Handbook of Organic Chem. Reg. No. 751834 1988 Mavoungou Gomes.
Beilstein Handbook of Organic Chem. Reg. No. 670954 1988 Mavoungou Gomes.
Beilstein Handbook of Organic Chem. Reg. No. 649696 1988 Dokunikhin.
Beilstein Handbook of Organic Chem. Reg. No. 530731 1988 Dokunichin.
Beilstein Handbook of Organic Chem. Reg. No. 660681 1988 Dokunichin.
Beilstein Handbook of Organic Chem. Reg. No. 4483194 1991 Oleinik.
Beilstein Handbook of Organic Chem. Reg. No. 4494786 1991 Oleinik.
Beilstein Handbook of Organic Chem. Reg. No. 3140506 1998.
Beilstein Handbook of Organic Chem. Reg. No. 56052 1998.
Beilstein Handbook of Organic Chem. Reg. No. 332938 1998.
Beilstein Handbook of Organic Chem. Reg. No. 254129 1998.
Beilstein Handbook of Organic Chem. Reg. No. 245245 1998.
Beilstein Handbook of Organic Chem. Reg. No. 244756 1998.
Beilstein Handbook of Organic Chem. Reg. No. 222316 1998.
Beilstein Handbook of Organic Chem. Reg. No. 207532 1998.
Beilstein Handbook of Organic Chem. Reg. No. 207516 1998.
Beilstein Handbook of Organic Chem. Reg. No. 165349 1998.
Beilstein Handbook of Organic Chem. Reg. No. 161148 1998.
Beilstein Handbook of Organic Chem. Reg. No. 2213597 1999.
Beilstein Handbook of Organic Chem. Reg. No. 13823 1999.
Biochem. J. 185, 775–77 1980 Purnell et al.
Biochemical and Biophysical Research Communications 136(3), 1110–15 1986 Tanuma et al.
Biochemical and Biophysical Research Communications 195, No. 2, 558–564 1993 Jesser et al.
Biochemical and Biophysical Research Communications 195(2), 558–64 1993 Jesser et al.
Biochemical and Biophysical Research Communications 210, No. 2, 329–337 1995 Aoki et al.
Biochemical and Biophysical Research Communications 220, 411–17 1996 Uchiumi et al.
Biochemical and Biophysical Research Communications 236, 265–69 1997 Maruta et al.
Biochemical and Biophysical Research Communications 245, 1–10 1998 Rhun et al.
Biochemical and Biophysical Research Communications 278(3) Nov. 30, 2000, 590–598 Zhang et al.
Biochemical Society Transactions vol. 8 (2), 1992–1993 1980 Whitby et al.
Biochemical Society Transactions 21:330–334 1993 Beckman et al.
Biochemistry 30, 5907–5912 1991 Maruta et al.
Biochemistry International 16, No. 3, 397–403 1988 Concha et al.
Biochemistry International 19, No. 6, 1395–1402 1989 Tanuma et al.
Biochemistry International 18, No. 4, 701–708 1989 Tanamua et al.
Biochemistry International 24, No. 5, 889–897 1991 Tsai et al.
Biochimica et Biophysica Acta 827, 228–234 1985 Tavassoli et al.
Biochimica et Biophysica Actas 1158, 251–56 1993 Aoki et al.
Biochimie vol. 77 No. 6, pp. 408–422 1995 Griffin et al.
Br. J. Pharm. 117:619–32 1996 Southan et al.
Brain Res. 710:169–77 1996 Wallis et al.
Brain Res. 729:264–69 1996 Cosi et al.
Brain Research 809:58–67 1998 Cosi et al.
Brain 122,247–253 1999 Love et al.
Brit. J. Pharm. 122:493–503 1997 Cuzzocrea.
Bull. Chem. Soc. Jpn. 61(6):2238–40 1998 Sato et al.
Bull. Soc. Chim. Fr. 233 1962 Granger et al.
C. R. Acad. Sci. 275:17, 961–64 1972 Michailidis et al.
Can J. Chem. 73, 319–35 1995 Desilets et al.
Cell 94, 325–337 1998 Kuida et al.
Cell 94, 339–352 1998 Hakem et al.
Cell Biology and Toxicology 9, No. 2, 165–175 1993 Clayson et al.
Cerebrovascular Disease 319–25 1997 Dawson et al.
Chem Abstracts 52:17 (14606h) (Sep. 10, 1958) Ochiai et al.
Chem Abstracts 55:6 (5491ce) (Mar. 20, 1961) Ochiai et al.
Chem Abstracts 58:4 (3425d) (Feb. 18, 1963) Hayashi et al.

Chem Abstracts vol. 126,No. 17,229493f (Apr. 28, 1997) Angeliki.
Chem. Abstracts 64:695e 1966 Ried et al.
Chem. Ber. 46,p. 2087, 2089 1993 Kadros.
Chemical Abstract 54:22648a 1954 Nikitskaya et al.
Chemical Abstract vol. 51:1960 1957 Taylor et al.
Chemical Abstract vol. 52:5846a 1958 Schmidt–Nickels.
Chemical Abstract vol. 52:6285 1958 Ohta.
Chemical Abstract vol. 52:4646 1958 Gilman et al.
Chemical Abstract vol. 52:5846b 1958 Gateff et al.
Chemical Abstract vol. 54:22647 1960 Campbell.
Chemical Abstract vol. 55:12868a 1961.
Chemical Abstract vol. 55:12868b 1961.
Chemical Abstract vol. 55:12868c 1961.
Chemical Abstract vol. 58:7884 1993 Sieglitz.
Chemical Abstract vol. 59:10037b 1963 Dokunikhin et al.
Chemical Abstract vol. 59:10037c 1963 Hazard et al.
Chemical Abstract vol. 61:15194 1964 Tsuboi.
Chemical Abstract vol. 61:13305h 1964 Quelet.
Chemical Abstract vol. 61:9493g 1964 Dokunikhin et al.
Chemical Abstract vol. 61:9494a 1964 Dokunikhin et al.
Chemical Abstract vol. 61:9493f 1964 Bodea et al.
Chemical Abstract vol. 61:13305g 1964 Badger et al.
Chemical Abstract vol. 63:7006 1965 Perrin.
Chemical Abstract vol. 62:5259 1965 Lakeside Lab., Inc.
Chemical Abstract vol. 62:9129e 1965 Kuehn.
Chemical Abstract vol. 63:4256 1965 Keene et al.
Chemical Abstract vol. 62:9129g 1965 Klosa.
Chemical Abstract vol. 65:15320a 1966 Kametani.
Chemical Abstract vol. 64:3526h 1966 Crossland.
Chemical Abstract vol. 65:15319h 1966 Humber et al.
Chemical Abstract vol. 69:87767 1968 Hofer.
Chemical Abstract vol. 68:59420 1968 Chandler et al.
Chemical Abstract vol. 70:3629 1969 Weis.
Chemical Abstract vol. 70:67988 1969 Resplandy et al.
Chemical Abstract vol. 70:115926 1969 Hofer.
Chemical Abstract vol. 70:4079 1969 Coyne et al.
Chemical Abstract vol. 73:35200 1970 Pan et al.
Chemical Abstract vol. 72:121337 1970 Pan et al.
Chemical Abstract vol. 74:111797 1971 Mavoungou–Gomes.
Chemical Abstract vol. 75:98422 1971 Campbell.
Chemical Abstract vol. 74:110112y (p. 252 May 10) 1971 Damas.
Chemical Abstract vol. 77:61927 1972 Zinchenko.
Chemical Abstract vol. 76:14566 1972 Rodway.
Chemical Abstract vol. 76:85774 1972 Mavoungou–Gomes.
Chemical Abstract vol. 78:123624 1973 Swenton et al.
Chemical Abstract vol. 78:68700 1973 Roehm et al.
Chemical Abstract vol. 78:58193 1973 Mondon et al.
Chemical Abstract vol. 78:84227 1973 Kraatz et al.
Chemical Abstract vol. 78:29384 1973 Forrester et al.
Chemical Abstract vol. 78:29593 1973 Cerbai et al.
Chemical Abstract vol. 81:37489 1974 Cerbai et al.
Chemical Abstract vol. 81:37417 1974 Baddar.
Chemical Abstract vol. 82:171011 1975 Rodway.
Chemical Abstract vol. 82:170471 1975 Mavoungou–Gomes.
Chemical Abstract vol. 83:27978 1975 Baddar.
Chemical Abstract vol. 84:42754 1976 Zaitsev.
Chemical Abstract vol. 84:3986 1976 Zaitsev.
Chemical Abstract vol. 85:182 1976 Tullar et al.
Chemical Abstract vol. 84:16943 1976 Minatoya et al.
Chemical Abstract vol. 85:77216 1976 Ege et al.
Chemical Abstract vol. 84:4857 1976 Cookson.
Chemical Abstract vol. 85(1976)159898a 1976.
Chemical Abstract vol. 86:171282 1977 Humber.
Chemical Abstract vol. 87:152015 1977 Houlihan.
Chemical Abstract vol. 87:5778 1977 Fomenko et al.
Chemical Abstract vol. 82:30602 1978 Minatoya et al.
Chemical Abstract vol. 90:6486t 1979 Takahashi.
Chemical Abstract vol. 91:39035 1979 Migachev.
Chemical Abstract vol. 90:38734 1979 Mavoungou–Gomes.
Chemical Abstract vol. 92:181104e 1980 Ryabukhina et al.
Chemical Abstract vol. 92:146482 1980 Rokach.
Chemical Abstract vol. 92:41620 1980 Migachev et al.
Chemical Abstract vol. 92:41511 1980 Migachev et al.
Chemical Abstract vol. 93:26178 1980 Gomes.
Chemical Abstract vol. 92:198336 1980 Cabares.
Chemical Abstract vol. 92:22393 1980 Simmonds.
Chemical Abstract vol. 95:80661 1981 Narasimhan et al.
Chemical Abstract vol. 95 (9):80666 1981 Migachev et al.
Chemical Abstract vol. 95:80688 1981 Migachev et al.
Chemical Abstract vol. 95:42867 1981 Migachev et al.
Chemical Abstract vol. 5:42866 1981 Migachev et al.
Chemical Abstract vol. 95:187120 1981 Migachev et al.
Chemical Abstract vol. 95:168911 1981 Houlihan.
Chemical Abstract vol. 96:6539m, p. 592 1982 Singh et al.
Chemical Abstract vol. 96:68519 1982 Leardini et al.
Chemical Abstract vol. 97:38635 1982 Krepelka.
Chemical Abstract vol. 97:126680 1982 Grimshaw et al.
Chemical Abstract vol. 100:103453 1984 Prostakov et al.
Chemical Abstract vol. 100:191713 1984 Orlic–Nuber et al.
Chemical Abstract vol. 100:139054 1984 Oleinik.
Chemical Abstract vol. 102:203854 1985 Migachev et al.
Chemical Abstract vol. 105:60505 1986 Andrievskii et al.
Chemical Abstract vol. 106 (67553) 1987 Pellefier.
Chemical Abstract vol. 107:23262 1987 Cabares.
Chemical Abstract vol. 107:39655v 1987 Bondarenko et al.
Chemical Abstract vol. 108:21627 1988 Duval.
Chemical Abstract vol. 110:230971 1989 Val'kova et al.
Chemical Abstract vol. 113:190649 1990 Val'kova et al.
Chemical Abstract vol. 112:44716 1990 Korl'kova et al.
Chemical Abstract vol. 112:128235 1990 Korol'kova et al.
Chemical Abstract vol. 112:216749 1990 Benson et al.
Chemical Abstract vol. 114: 143456 1991 Walser.
Chemical Abstract vol. 115 (232107) 1991 Nagao.
Chemical Abstract vol. 115:70731f 1991 Donshikh et al.
Chemical Abstract vol. 115:158338 1991 Buckman et al.
Chemical Abstract vol. 114:42543 1991 Andrievskii et al.
Chemical Abstract vol. 119:72127 1993 Zaitsev et al.
Chemical Abstract vol. 118:191567 1993 Dow.
Chemical Abstract vol. 118:80722 1993 Dininno et al.
Chemical Abstract vol. 118:101709 1993 Dininno et al.
Chemical Abstract vol. 120:134231 1994 Rocca et al.
Chemical Abstract vol. 121:220651v 1994 Pawlowska et al.
Chemical Abstract vol. 121:172572 1994 Liu et al.
Chemical Abstract vol. 120:95793 1994 Kyota et al.
Chemical Abstract vol. 121:57315 1994 Dow et al.
Chemical Abstract vol. 120:148508p 1994 Barros et al.
Chemical Abstract vol. 123:505 1995 Weltin et al.
Chemical Abstract vol. 122:10865 1995 Lamba et al.
Chemical Abstract vol. 122:170499 1995 Korol'kova et al.
Chemical Abstract vol. 123:256711 1995 Kalindjian et al.
Chemical Abstract vol. 122:170250 1995 Gorio et al.
Chemical Abstract vol. 122:187249 1995 Dininno et al.
Chemical Abstract vol. 122:316902 1995 Desilets et al.
Chemical Abstract vol. 122:316901 1995 Desilets et al.

Chemical Abstract vol. 122:187526 1995 Langlois et al.
Chemical Abstract vol. 125:87882 1996 Yamaguchi et al.
Chemical Abstract vol. 124:331706 1996 Silverman et al.
Chemical Abstract vol. 124:131261 1996 Richter.
Chemical Abstract vol. 126:115554 1996 Malhotra et al.
Chemical Abstract vol. 125:246943 1996 Korol'kova et al.
Chemical Abstract vol. 125:277462 1996 Ge et al.
Chemical Abstract vol. 124:202047 1996 Fernandez et al.
Chemical Abstract vol. 128:36109 1997 Sakai et al.
Chemical Abstract vol. 127:234258 1997 Reddy et al.
Chemical Abstract vol. 127:81282 1997 Marek et al.
Chemical Abstract vol. 128:34752 1997 Jones et al.
Chemical Abstract vol. 127:80243 1997 Banister et al.
Chemical Abstract abstract No. 17462 1998 Yoshida et al.
Chemical Abstract vol. 129:104224 1998 West.
Chemical Abstract vol. 138099 1998 Weltin et al.
Chemical Abstract vol. 130:24816 1998 Park et al.
Chemical Abstract vol. 128:75320 1998 Jones et al.
Chemical Abstract vol. 128:165850 1998 Cookson et al.
Chemical Abstract vol. 129:54301 1998 Albright et al.
Chemical Abstract No. 816103 1998 Albright et al.
Chemical Abstracts vol. 52 (21) 18420d 1958 Tanida.
Chemical Abstracts vol. 62, No. 5, 5271c Mar. 1965.
Chemical Abstracts vol. 76 (25) 153704b 1972 Pozharskii et al.
Chemical Abstracts vol. 88 (7) 49887 1978 Szadowski.
Chemical Abstracts vol. 88, No. 13, 5 05 (88:89502c) 1978 Dokunikhin et al.
Chemical Abstracts vol. 94, No. 23, 637(192098y) 1981 Migachev.
Chemical Abstracts Registry No. 17 1399–15–8 1998.
Chemical Abstracts Registry No. 14223 8–47–9 1998.
Chemical Abstracts 85:159898a 85, No. 21, 521 1974 Upadysheva et al.
Chemical and Pharmaceutical Bulletin vol. 26, No. 12, pp. 3682–3694 1978 Hamada et al.
Chemische Berichte vol. 102, 1161–1176 1969 Kauffmann et al.
Eur. J. Biochem. vol. 244, pp. 15–20 1997 Van Gool et al.
Eur. J. Med Chem. 29, 925–40 1994 Langlois et al.
Eur. J. Pham. 204, 339–40 1991 Nowicki et al.
Gazz. Chim. Ital. 91:1345–51 1962 Di Maio et al.
Gazz Chim. Ital. 91:1124–32 1962 Di Maio et al.
Gazz. Chim. Ital. 94:590–94 1964 Di Maio et al.
Hawleys Chemical Condense Dictionary Sax (Ed) 11th Ed, 1987 p. 898 1987 Hawley's.
Heterocycles 22:2, 237–40 1984 Naito et al.
Int. J. Immunopharmac 17, No. 4, 265–271 1995 Wetlin et al.
Int. J. Radiat. Biol. vol. 72 No. 6, pp. 685–692 1997 Wetlin et al.
Int. J. Radiat. Biol. Relat. Stud. Phys. Chem. Med. vol. 48 No. 5, pp. 675–690 1985 Harris.
Intl. J. Oncol 8:239–52 1996 Bauer et al.
IPER for PCT/US98/18189.
IS&T'sTenth Intl'l Congress on Advances in Non–Impact Printing Technologies 246–248 1994 Richter.
ISR for PCT/US99/30979.
Itsu Kenkusho Nempo 16:15–23 1971 Ochiai et al.
J Cerebral Flood Flow Metabol. 17(11): 1143–51 1997 Endres et al.
J Chem. Soc. 11:1293–97 1978 Davies et al.
J. Am. Chem. Soc. 78:5104–8 1956 Taylor et al.
J. Biol. Chem 270:19, 11176–80 1995 Heller et al.
J. Biol. Chem. 246(20). 6362–64 1972 Miwa et al.
J. Biol. Chem. 261(32), 14902–11 1986 Hatakeyama et al.
J. Biol. Chem. 262(36), 17641–50 1987 Ikejima et al.
J. Biol. Chem. 263(23), 11037–40 1988 Ikejima et al.
J. Biol. Chem. 267(20), 14436–42 1992 Tsai et al.
J. Biol. Chem. 267:3, 1569–75 1992 Banasik et al.
J. Biol. Chem. 272:9030–36 1997 Szabó et al.
J. Chem Soc. 12:2231–2241 1971 Barton.
J. Chem. Res., Synop. 8:302 1992 Mueller et al.
J. Chem. Res., Synop. 2:126 1996 Mueller et al.
J. Chem. Soc. pp. 1979–1984 1929 Blount et al.
J. Chem. Soc. 1624–28 1958 Johnson.
J. Chem. Soc. 4295–98 1962 Brown et al.
J. Chem. Soc. 1:14, 1747–51 1974 Nnomiya et al.
J. Chem. Soc. 1:7, 763–70 1974 Bailey et al.
J. Exp Med. vol. 186, No. 7, Oct. 6, 1997, 1041–9 1997 Szabo.
J. Het. Chem vol. 7, pp. 597–605 1970 Pan et al.
J. Heterocycl. Chem. 20:5, 1407–9 1983 Rougeot et al.
J. Immuno. 153:3319–25 1994 Hughes et al.
J. Med. Chem. 38, 389–393 1995 Slama et al.
J. Med. Chem. 38, 4332–4336 1995 Slama et al.
J. Neurochem 65:3, 1411–14 1995 Zhang et al.
J. Neurosci 13:6, 2651–61 1993 Dawson et al.
J. Neurosci. 16:8, 2479–87 1996 Dawson et al.
J. Neuroscience Res. 47: 372–383 1997 Ceruti et al.
J. of Biological Chemistry 261(2), 965–69 1986 Tanuma et al.
J. Org Chem. 29;3, 681–55 1964 Masamune et al.
J. Org Chem. 47, 2043–2047 1982 Taylor et al.
J. Org. Chem. vol. 23, pp. 1071–1072 Jul. 1958 Robinson et al.
J. Org. Chem. 29:11, 3180–85 1964 Baer et al.
J. Org. Chem. 43:11, 2190–96 1978 Eisch et al.
J. Urol. vol. 150, pp. 1526–1532 1993 Sklar et al.
JACS 71:937–8 (Mar. 1949) Wilson et al.
JACS 76:4396–8 (Sep. 5, 1954) Wright.
Japanese J. Pharm. 75, Supp. I:102 1997 Szabó et al.
Japanese J. Pharm. 75, Supp. I:15 1997 Salzman et al.
JCS pp. 4067–75 1952 Peak et al.
JCS pp. 1294–1304 1956 Albert et al.
JCS pp. 2384–2396 1959 Albert et al.
Journal of Cellular Biochemistry 29:361–372 1985 Bolander, Jr.
Journal of Cerebral Blood Flow and Metabolism 17 No. 11, 1137–1142 1997 Takahashi et al.
Journal of Heterocyclic Chemistry vol. 3, pp. 466–469 Dec. 1966 Aparajithan.
Journal of Heterocyclic Chemistry vol. 15, pp. 1513–1514 1978 Nuvole et al.
Journal of Medicinal Chemistry vol. 20 (3) 449–452 1977 Diana et al.
Journal of Neurochemistry 70, No. 2, 501–508 1998 Cookson et al.
Journal of Organic Chemistry vol. 11, No. 3, 239–246 1946 Bergstrom et al.
Journal of Organic Chemistry 53(20):4650–3 1988 D. Dumas.
Journal of the Chemical Society pp. 1799–1803 1972 Singh et al.
Journal of the Chemistry Society vol. 9, 944–950 1976 Lowenthal et al.
Justus Liebigs Ann. Chem. 388, p. 212 1912 Ullmann et al.
Med Chem. Res. 6:2, 81–101 1996 Castan et al.

Molec. Cell. Biochem. 138:185–97 1994 Banasik et al.
Mutation Research 218, 67–74 1989 Gonzalez et al.
Mutation Research 350, 25–34 1996 Wachsman.
Nature Medicine JHU 1997 Eliasson et al.
Neuron 1, 623–634 1988 Choi.
NeuroReport 5:3, 245–48 1993 Wallis et al.
Nucleic Acids Research 29(3) 841–849 2001 Simbulan–Rosenthal et al.
Oncol. Res. 6:9, 399–403 1994 Weltin et al.
Pain vol. 72, pp. 355–366 1997 Mao et al.
Pharm. Bull. 5:289–91 1957 Ochiai et al.
Phosphorus Sulfur vol. 14, No. 1, pp. 131–138 1983 Becher et al.
Proc. Natl. Acad Sci. USA 88:6368–71 1991 Dawson et al.
Proc. Natl. Acad Sci. USA 93:1753–58 1996 Szabó et al.
Proc. Natl. Acad Sci. USA 94:679–83 1997 Thiemermann et al.
Proc. Natl. Acad. Sci. USA vol. 93, pp. 7481–7485 1996 Ruf et al.
Proc. Natl. Acad. Sci. USA 96:5774–5779 (May 1999) Mandie et al.
Radiat Res. vol. 116 No. 3, pp. 442–452 1988 Paaphorst et al.
Radiat Res. 101:29–46 1985 Oleinik.
Res. Comm. Mol. Pathol. Pharmacol. vol. 95 No. 3, pp. 241–252 1997 Lam.
Ric Sci. 38:3, 231–33 1968 Di Maio et al.
Rocz. Chem. 41:1,89–101 1967 Schoen et al.
Science 223:589–91 1984 Milam et al.
Science 263:687–89 1994 Zhang et al.
Science 265:1883–1885 1994 Huang et al.
Science 282, 1484–1487 1998 Smith et al.
Shock 5(4):258–64 1996 Zingarelli et al.
Spin Label Analogue of ATP 246, No. 20, 6362–6364 1971 Miwa et al.
Switzerland Patent 601 246 1978.
Terato., Carcino., and Muta. 16:219–27 1996 Cristovao et al.
Tetrahedron supp. 8, part 1, pp. 305–312 1966 Tamayo et al.
Tetrahedron Letters 32,No. 35, 4525–4528 1991 Chida et al.
Tetrahedron Letters 36:33, 5983–66 1995 White et al.
Tetrahedron Letters 52:9, 3117–34 1996 White et al.
The EMBO Journal vol. 16 No. 19, pp. 6018–6033 1997 Vaziri et al.
The Journal of Biological Chemistry 242, No. 22, 5301–5307 1967 Futai et al.
The Journal of Biological Chemistry vol. 257, NO. 21, 12872–12877 1982 Wielckens et al.
The Journal of Biological Chemistry 259, No. 2, 986–995 1984 Oka et al.
The Journal of Biological Chemistry 261, No. 2, pp. 965–969 1986 Tanuma et al.
The Journal of Biological Chemistry 263, No. 23, 11037–11040 1988 Ikejima et al.
The Journal of Biological Chemistry 272, No. 18, 11895–11901 1997 Lin et al.
TiPS 11, 379–387 1990 Meldrum et al.
TiPS in press 1998 Pieper et al.
Trends Neurosci. 20:3, 132–139 1997 Iadecola.
Vertex Phamaceuticals Inc. PR Newswire 1998.
U.S. application No. 08/922,520, 1997, Jackson et al., abandoned.
U.S. application No. 08/922,575, 1997, abandoned.
U.S. application No. 08/922,548, 1997, pending.
U.S. application No. 09/387,767, 1999, Li et al., pending.
U.S. application No. 09/224,294, 1999, Zhang et al.
U.S. application No. 09/224,293, 1998, Zhang et al., pending.
U.S. application No. 09/145,180, 1998, Li et al., pending.
U.S. application No. 09/145,184, 1998, Li et al., pending.
U.S. application No. 09/145,181, 1998, Li et al., pending.
U.S. application No. 09/079,514, 1998, Li et al., abandoned.
U.S. application No. 09/079,510, 1998, Li et al., abandoned.
U.S. application No. 09/079,509, 1998, Li et al., abandoned.
U.S. application No. 09/079,502 1998, Li et al., allowed.
U.S. application No. 09/145,185, 1998, Jackson et al.
U.S. application No. 09/145,179, 1998, Jackson et al., pending.
U.S. application No. 09/145,178, 1998, Jackson et al., pending.
U.S. application No. 09/145,177, 1998, Jackson et al., abandoned.
U.S. application No. 09/145,176, 1998, Jackson et al., pending.
U.S. application No. 09/145,166, 1998, Jackson et al.
U.S. application No. 09/079,513, 1998, Jackson et al., abandoned.
U.S. application No. 09/079,512, 1998, Jackson et al., abandoned.
U.S. application No. 09/689,942, 1998, Jackson et al., pending.
U.S. application No. 09/079,511, 1998, Jackson et al., abandoned.
U.S. application No. 09/079,508, 1998, Jackson et al., pending.
U.S. application No. 09/079,507, 1998, Jackson et al., abandoned.
Zhang et al., "Nitric Oxide Activation of Poly(ADP–ribose) Synthetase in Neurotoxicity," *Science*, 263:687–89 (1994).
Wallis et al., "Neuroprotection Against Nitric Oxide Injury with Inhibitors of ADP–ribosylation," *NeuroReport*, 5:3, 245–48 (1993).
Endres et al., "Ischemic Brain Injury is Mediated by the Activation of Poly(ADP–Ribose) Polymerase," *J. Cerebral Flow Metabol.*, 17(11):1143–51 (1997).
Wallis et al., Traumatic Neuroprotection with Inhibitors of Nitric Oxide and ADP–Ribosylation, *Brain Res.*, 710:169–77 (1996).
Thiemermann et al., "Inhibition of the Activity of Poly(ADP Ribose) Synthetase Reduces Ischemia–Reperfusion Injury in the Heart and Skeletal Muscle", *Proc. Natl. Acad. Sci. USA*, 94:679–83 (1997).
Zhang et al., "Poly(ADP–Ribose) Synthetase Activation: An Early Indicator of Neurotoxic DNA Damage", *J. Neurochem.*, 65:3, 1411–14 (1995).
Cosi et al., "Poly(ADP–Ribose) Polymerase (PARP) Revisited. A New Role for an Old Enzyme: PARP Involvement in Neurodegeneration and PARP Inhibitors as Possible Neuroprotective Agents", *Ann. N. Y. Acad. Sci.*, 825:366–79 (1997).
Cosi et al., "Poly(ADP–Ribose) Polymerase Inhibitors Protect Against MPTP–induced Depletions of Striatal Dopamine and Cortical Noradrenaline in C57Bl/6 Mice", *Brain Res.*, 729:264–69 (1996).
Dawson et al., "Protection of the Brain from Ischemia", *Cerebrovascular Disease*, 319–25 (H. Hunt Batjer ed., 1997).

Dawson et al., "Nitric Oxide Mediates Glutamate Neurotoxicity in Primary Cortical Cultures", *Proc. Natl. Acad. Sci. USA*, 88:6368–71 (1991).

Dawson et al., "Mechanisms of Nitric Oxide–mediated Neurotoxicity in Primary Brain Cultures", *J. Neurosci.*, 13:6, 2651–61 (1993).

Dawson et al., "Resistance to Neurotoxicity in Cortical Cultures from Neuronal Nitric Oxide Synthase–Deficient Mice", *J. Neurosci.*, 16:8, 2479–87 (1996).

Iadecola, "Bright and Dark Sides of Nitric Oxide in Ischemic Brain Injury", *Trends Neurosci.*, 20:3, 132–39 (1997).

Huang et al., "Effects of Cerebral Ischemia in Mice Deficient in Neuronal Nitric Oxide Synthase", *Science*, 265:1883–85 (1994).

Beckman et al., "Pathological Implications of Nitric Oxide, Superoxide and Peroxynitrite Formation", *Biochem. Soc. Trans.*, 21:330–34 (1993).

Szabó et al., "DNA Strand Breakage, Activation of Poly-(ADP–Ribose) Synthetase, and Cellular Energy Depletion are Involved in the Cytotoxicity in Macrophages and Smooth Muscle Cells Exposed to Peroxynitrite", *Proc. Natl. Acad. Sci. USA*, 93:1753–58 (1996).

Cosi et al., Poly(ADP–Ribose)Polymerase Inhibitors Protect Against MPTP–induced Depletions of Striatal Dopamine and Cortical Noradrenaline in C57B1/6 Mice, *Brain Res.*, 729:264–69 (1996).

Cristovao et al., "Effect of a Poly(ADP–Ribose) Polymerase Inhibitor on DNA Breakage and Cytotoxicity Induced by Hydrogen Peroxide and γ–Radiation", *Terato., Carcino., and Muta.*, 16:219–27 (1996).

Salzman et al., "Role of Peroxynitrite and Poly(ADP–Ribose) Synthase Activation Experimental Colitis", *Japanese J. Pharm.*, 75, Supp. I:15 (1997).

Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", *Br. J. Pharm.*, 117:619–32 (1996).

Szabó et al., "Mercaptoethylguanidine and Guanidine Inhibitors of Nitric Oxide Synthase React with Peroxynitrite and Protect Against Peroxynitrite–induced Oxidative Damage", *J. Biol. Chem.*, 272:9030–36 (1997).

Szabó et al., "Protective Effects of an Inhibitor of Poly(ADP–Ribose)Synthetase in Collagen–Induced Arthritis," *Japanese J. Pharm.*, 75, Supp. I:102 (1997).

Bauer et al., "Modification of Growth Related Enzymatic Pathways and Apparent Loss of Tumorigenicity of a ras–transformed Bovine Endothelial Cell Line by Treatment with 5–Iodo–6–amino–1,2–benzopyrone (INH$_2$BP)", *Intl. J. Oncol.*, 8:239–52 (1996).

Hughes et al., "Induction of T Helper Cell Hyporesponsiveness in an Experimental Model of Autoimmunity by Using Nonmitogenic Anti–CD3 Monoclonal Antibody", *J. Immuno.*, 153:3319–25 (1994).

Heller et al., "Inactivation of the Poly(ADP–Ribose) Polymerase Gene Affects Oxygen Radical and Nitric Oxide Toxicity in Islet Cells", *J. Biol. Chem.*, 270:19, 11176–80 (May 1995).

Zingarelli et al., "Protective Effects of Nicotinamide Against Nitric Oxide–Mediated Delayed Vascular Failure in Endotoxic Shock: Potential Involvement of PolyADP Ribosyl Synthetase", *Shock*, 5:258–64 (1996).

Cuzzocrea, "Role of Peroxynitrite and Activation of Poly-(ADP–Ribose) Synthetase in the Vascular Failure Induced by Zymosan–activated Plasma", *Brit. J. Pharm.*, 122:493–503 (1997).

Suto et al., "Dihydroisoquinolinones: The Design and Synthesis of a New Series of Potent Inhibitors of Poly(ADP–Ribose) Polymerase", *Anticancer Drug Des.*, 7:107–17 (1991).

Weltin et al., "Effect of 6(5H)–Phenanthridinone, an Inhibitor of Poly(ADP–ribose) Polymerase, on Cultured Tumor Cells", *Oncol. Res.*, 6:9, 399–403 (1994).

Banasik et al., "Specific Inhibitors of Poly(ADP–Ribose) Synthetase and Mono(ADP–Ribosyl)–Transferase", *J. Biol. Chem.*, 267:3, 1569–75 (1992).

Banasik et al., "Inhibitors and Activators of ADP–Ribosylation Reactions", *Molec. Cell. Biochem.*, 138:185–97 (1994).

Milam et al., "Inhibitors of Poly(Adenosine Diphosphate–Ribose) Synthesis: Effect on Other Metabolic Processes", *Science*, 223:589–91 (1984).

White et al, "Quinoline Analogues of Ortho–Quinodimethane," *Tetrahedron Letters*, 36:33, 5983–86 (1995).

White et al., "Dihydrothiophenes as Precursors to Fused Quinolines, Quinolones and Coumarins via o–Quinodimethane Intermediates," *Tetrahedron Letters*, 52:9, 3117–34 (1996).

A. Albert & J.N. Phillips, "Ionization Constants of Heterocyclic Substances. Part II. Hydroxy–derivatives of Nitrogenous Six–membered Ring–compounds", *Journal of the Chemical Society*, pp. 1294–304 (1956).

M. Banasik et al., "Specific Inhibitors of Poly(ADP–Ribose) Synthetase and Mono(ADP–Ribosyl) transferase", *Journal of Biological Chemistry*, 267(3):1569–75 (Jan. 25, 1992).

Chemical Abstracts, vol. 52, No. 17, abstract No. 14606h (Sep. 10, 1958).

Chemical Abstracts, vol. 55, No. 6, abstract No. 5491ce (Mar. 20, 1961).

Chemical Abstracts, vol. 58, No. 4, abstract No. 3425d (Feb. 18, 1963).

R. Griffin et al., "Novel Potent Inhibitors of the DNA Repair Enzyme Poly(ADP–Ribose) Polymerase (PARP)", *Anti–Cancer Drug Design*, 10(6):507–14 (Sep. 1995).

A. Nuvole & G. Pinna, "Synthesis of 1–Amino–4chloroisoquinoline. A New Approach to 1–Aminoisoquinoline", *Journal of Heterocyclic Chemistry*, vol. 15, pp. 1513–4 (Dec. 1978).

M.J. Suto et al., "Dihydroisoquinolinones: The Design and Synthesis of a New Series of Potent Inhibitors of Poly(ADP–Ribose) Polymerase", *Anti–Cancer Drug Design*, vol. 7, pp. 107–17 (1991).

E. Taylor et al., "Nucleophilic Displacement of Primary Amino Groups via 1–Substituted 4 Tosylimidazoles", *Journal of Organic Chemistry*, 47(11):2043–6 (1982).

J. Wilson et al., "Local Anesthetics. Aminoalkoxyisoquinoline Derivatives", *Journal of the American Chemical Society*, vol. 71, pp. 937–8 (Mar. 1949).

H. Wright & M.B. Moore, "Local Anesthetics. V. 4–Morpholinylalkyl Aryl Ether", *Journal of the American Chemical Society*, vol. 76, pp. 4396–8 (Sep. 5, 1954).

* cited by examiner

ALKOXY-SUBSTITUTED COMPOUNDS, METHODS AND COMPOSITIONS FOR INHIBITING PARP ACTIVITY

This application is a continuation in part of Ser. No. 08/922,520, filed Sep. 3, 1997.

BACKGROUND OF THE INVENTION

1. Field of the Invention

The invention relates to inhibitors of the nucleic enzyme poly(adenosine 5'-diphospho-ribose) polymerase ["poly (ADP-ribose) polymerase" or "PARP", which is also sometimes called "PARS" for poly(ADP-ribose) synthetase]. More particularly, the invention relates to the use of PARP inhibitors to prevent and/or treat neural tissue damage resulting from ischemia and reperfusion injury, neurological disorders and neurodegenerative diseases; to prevent or treat vascular stroke; to treat or prevent cardiovascular disorders; or to treat other disorders such as arthritis; diabetes; septic shock (such as endotoxic shock); inflammatory bowel disorders (such as colitis and Crohn's disease); and cancer.

2. Description of the Prior Art

Poly(ADP-ribose) polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been fully established, this enzyme is thought to play a role in enhancing DNA repair.

During major cellular stresses, however, the extensive activation of PARP can rapidly lead to cell death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

It has been reported that PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose) Synthetase in Neurotoxicity", Science, 263:687–89 (1994); and in hippocampal slices (Wallis et al., "Neuroprotection Against Nitric Oxide Injury with Inhibitors of ADP-Ribosylation", NeuroReport, 5:3, 245–48 (1993). The potential role of PARP inhibitors in treating neurodegenerative diseases and head trauma has thus been known. Research, however, continues to pinpoint the exact mechanisms of their salutary effect in cerebral ischemia, (Endres et al., "Ischemic Brain Injury is Mediated by the Activation of Poly(ADP-Ribose)Polymerase", J. Cereb. Blood Flow Metabol., 17:1143–51 (1997)) and in traumatic brain injury (Wallis et al., "Traumatic Neuroprotection with Inhibitors of Nitric Oxide and ADP-Ribosylation, Brain Res., 710:169–77 (1996)).

It has been demonstrated that single injections of PARP inhibitors have reduced the infarct size caused by ischemia and reperfusion of the heart or skeletal muscle in rabbits. In these studies, a single injection of the PARP inhibitor, 3-amino-benzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", Proc. Natl. Acad. Sci. USA, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MPP$^+$), which participate in pathological conditions such as stroke, Alzheimer's disease and Parkinson's disease. Zhang et al., "Poly(ADP-Ribose) Synthetase Activation: An Early Indicator of Neurotoxic DNA Damage", J. Neurochem., 65:3, 1411–14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP Inhibitors as Possible Neuroprotective Agents", Ann. N. Y. Acad. Sci., 825:366–79 (1997) ; and Cosi et al., "Poly(ADP-Ribose) Polymerase Inhibitors Protect Against MPTP-induced Depletions of Striatal Dopamine and Cortical Noradrenaline in C57B1/6 Mice", Brain Res., 729:264–69 (1996).

Neural damage following stroke and other neurodegenerative processes is thought to result from a massive release of the excitatory neurotransmitter glutamate, which acts upon the N-methyl-D-aspartate (NMDA) receptors and other subtype receptors. Evidence includes findings in many animal species, as well as in cerebral cortical cultures treated with glutamate or NMDA, that glutamate receptor antagonists block neural damage following vascular stroke. Dawson et al., "Protection of the Brain from Ischemia", Cerebrovascular Disease, 319–25 (H. Hunt Batjer ed., 1997).

The stimulation of NMDA receptors, in turn, activates the enzyme neuronal nitric oxide synthase (NNOS), which causes the formation of nitric oxide (NO), which more directly mediates neurotoxicity. Protection against NMDA neurotoxicity has occurred following treatment with NOS inhibitors. See Dawson et al., "Nitric Oxide Mediates Glutamate Neurotoxicity in Primary Cortical Cultures", Proc. Natl. Acad. Sci. USA, 88:6368–71 (1991); and Dawson et al., "Mechanisms of Nitric Oxide-mediated Neurotoxicity in Primary Brain Cultures", J. Neurosci., 13:6, 2651–61 (1993). Protection against NMDA neurotoxicity can also occur in cortical cultures from mice with targeted disruption of NNOS. See Dawson et al., "Resistance to Neurotoxicity in Cortical Cultures from Neuronal Nitric Oxide Synthase-Deficient Mice", J. Neurosci., 16:8, 2479–87 (1996).

It is known that neural damage following vascular stroke is markedly diminished in animals treated with NOS inhibitors or in mice with NNOS gene disruption. Iadecola, "Bright and Dark Sides of Nitric Oxide in Ischemic Brain Injury", Trends Neurosci., 20:3, 132–39 (1997); and Huang et al., "Effects of Cerebral Ischemia in Mice Deficient in Neuronal Nitric Oxide Synthase", Science, 265:1883–85 (1994). See also, Beckman et al., "Pathological Implications of Nitric Oxide, Superoxide and Peroxynitrite Formation", Biochem. Soc. Trans., 21:330–34 (1993). Either NO or peroxynitrite can cause DNA damage, which activates PARP. Further support for this is provided in Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite", *Proc. Natl. Acad. Sci. USA*, 93:1753–58 (1996).

Zhang et al., U.S. Pat. No. 5,587,384, issued Dec. 24, 1996, discusses the use of certain PARP inhibitors, such as benzamide and 1,5-dihydroxy-isoquinoline, to prevent NMDA-mediated neurotoxicity and, thus, treat stroke, Alzheimer's disease, Parkinson's disease and Huntington's disease. However, it is has now been discovered that Zhang et al. may have been in error in classifying neurotoxicity as NMDA-mediated neurotoxicity. Rather, it may have been more appropriate to classify the in vivo neurotoxicity present as glutamate neurotoxicity. See Zhang et al. "Nitric Oxide Activation of Poly(ADP-Ribose) Synthetase in Neurotoxicity", *Science*, 263:687–89 (1994). See also, Cosi et al., Poly(ADP-Ribose)Polymerase Inhibitors Protect Against MPTP-induced Depletions of Striatal Dopamine and Cortical Noradrenaline in C57B1/6 Mice", *Brain Res.*, 729:264–69 (1996).

It is also known that PARP inhibitors effect DNA repair generally. Cristovao et al., "Effect of a Poly(ADP-Ribose) Polymerase Inhibitor on DNA Breakage and Cytotoxicity Induced by Hydrogen Peroxide and γ-Radiation," *Terato., Carcino., and Muta.*, 16:219–27 (1996), discusses the effect of hydrogen peroxide and γ-radiation on DNA strand breaks in the presence of and in the absence of 3-aminobenzamide, a potent inhibitor of PARP. Cristovao et al. observed a PARP-dependent recovery of DNA strand breaks in leukocytes treated with hydrogen peroxide.

Evidence also exists that PARP inhibitors are useful for treating inflammatory bowel disorders. Salzman et al., "Role of Peroxynitrite and Poly(ADP-Ribose)Synthase Activation Experimental Colitis," *Japanese J. Pharm.*, 75, Supp. I:15 (1997), discusses the ability of PARP inhibitors to prevent or treat colitis. Colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", *Br. J. Pharm.*, 117:619–32 (1996); and Szabó et al., "Mercaptoethylguanidine and Guanidine Inhibitors of Nitric Oxide Synthase React with Peroxynitrite and Protect Against Peroxynitrite-induced Oxidative Damage", *J. Biol. Chem.*, 272:9030–36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," *Japanese J. Pharm.*, 75, Supp. I:102 (1997), discusses the ability of PARP inhibitors to prevent or treat collagen-induced arthritis. See also Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite," *Proc. Natl. Acad. Sci. USA*, 93:1753–58 (March 1996); Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone (INH$_2$BP)", *Intl. J. Oncol.*, 8:239–52 (1996); and Hughes et al., "Induction of T Helper Cell Hyporesponsiveness in an Experimental Model of Autoimmunity by Using Nonmitogenic Anti-CD3 Monoclonal Antibody", *J. Immuno.*, 153:3319–25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells," *J. Biol. Chem.*, 270:19, 11176–80 (May 1995), discusses the tendency of PARP to deplete cellular NAD+ and induce the death of insulin-producing islet cells. Heller et al. used cells from mice with inactivated PARP genes and found that these mutant cells did not show NAD+ depletion after exposure to DNA-damaging radicals. The mutant cells were also found to be more resistant to the toxicity of NO.

Further still, PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," *Shock*, 5:258–64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose) synthetase. See also, Cuzzocrea, "Role of Peroxynitrite and Activation of Poly(ADP-Ribose) Synthetase in the Vascular Failure Induced by Zymosan-activated Plasma," *Brit. J. Pharm.*, 122:493–503 (1997).

Yet another known use for PARP inhibitors is treating cancer. Suto et al., "Dihydroisoquinolinones: The Design and Synthesis of a New Series of Potent Inhibitors of Poly(ADP-Ribose) Polymerase", *Anticancer Drug Des.*, 7:107–17 (1991), discloses processes for synthesizing a number of different PARP inhibitors. In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly (ADP-ribose) Polymerase, on Cultured Tumor Cells", *Oncol. Res.*, 6:9, 399–403 (1994), discusses the inhibition of PARP activity, reduced proliferation of tumor cells, and a marked synergistic effect when tumor cells are co-treated with an alkylating drug.

Large numbers of known PARP inhibitors have been described in Banasik et al., "Specific Inhibitors of Poly (ADP-Ribose) Synthetase and Mono(ADP-Ribosyl)-Transferase", *J. Biol. Chem.*, 267:3, 1569–75 (1992), and in Banasik et al., "Inhibitors and Activators of ADP-Ribosylation Reactions", *Molec. Cell. Biochem.*, 738:185–97 (1994).

However, the approach of using these PARP inhibitors to reduce NMDA-receptor stimulation, or to treat or prevent neural tissue damage caused by NO, ischemia and reperfusion of the heart or skeletal muscle, arthritis, diabetes, endotoxic or septic shock, inflammatory diseases of the bowel (such as colitis and Crohn's disease), and cancer, has been limited in effect. For example, side effects have been observed with some of the best-known PARP inhibitors, as discussed in Milam et al., "Inhibitors of Poly(Adenosine Diphosphate-Ribose) Synthesis: Effect on Other Metabolic Processes", *Science*, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose small enough to inhibit the enzyme without producing additional metabolic effects.

Accordingly, there remains a need for compounds that inhibit PARP activity and compositions and methods containing PARP inhibitors are more potent and reliable with fewer side effects, particularly with respect to vascular stroke.

Further, other multicyclic, nitrogen-containing, alkoxy-substituted compounds are known:
1,3-Dihydro-4-methoxy-thieno[3,4-c]quinoline, which has the following structure:

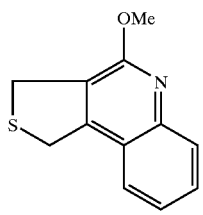

is disclosed in White et al., "Quinoline Analogues of Ortho-Quinodimethane," *Tetrahedron Letters,* 36:33, 5983–86 (1995). This structure is also disclosed in White et al., "Dihydrothiophenes as Precursors to Fused Quinolines, Quinolones and Coumarins via o-Quinodimethane Intermediates," *Tetrahedron Letters,* 52:9, 3117–34 (1996). Both of the White references also disclose the following structures:

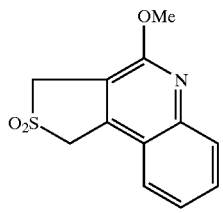 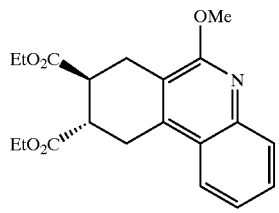

It is not believed that the above disclosed compounds have been shown to inhibit PARP activity per se.

SUMMARY OF THE INVENTION

The compounds of the invention have formula I:

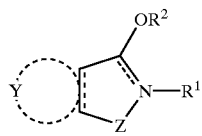

or a pharmaceutically acceptable salt, prodrug, metabolite, optical isomer or stereoisomer thereof, wherein:
  $R^1$, when present, is hydrogen or lower alkyl;
  $R^2$ is lower alkyl, aryl, aralkyl, lower alkanoyl, or —$(CH_2)_n$—$(CHOH)_y(CH_2)_m$A, wherein n is 1–4, y is 0 or 1, m is 0–5, and A is cycloalkyl, cycloalkenyl, lower alkanoyl, aryl, aralkyl, —$NH_2$, —NH-(lower alkyl),

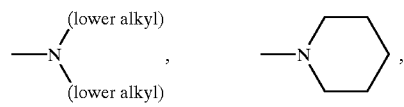

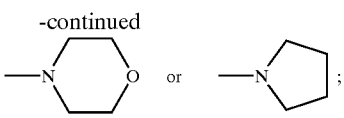

Y represents the atoms necessary to form a fused 5- to 6-membered ring that is aromatic or nonaromatic and carbocyclic or heterocyclic;
Z is
  (i) —$CHR^2CHR^3$— where $R^2$ and $R^3$ are independently hydrogen, alkyl, aryl or aralkyl;
  (ii) —$R^6C$=$CR^3$— where $R^6$ and $R^3$ are independently hydrogen, lower alkyl, aryl, aralkyl, chlorine, bromine or —$NR^7R^8$, where $R^7$ and $R^8$ are independently hydrogen or lower alkyl, or, $R^6$ and $R^3$, taken together, form a fused 5- to 6-membered ring that is aromatic or nonaromatic and carbocyclic or heterocyclic;
  (iii) —$R^2C$=N—;
  (iv) —$CR^2(OH)$—$NR^7$—; or
  (v) —$C(O)$—$NR^7$—;
provided that:
  when $R^6$ and $R^3$ form a fused benzene ring, then Y is neither (a) a fused, 6-membered, nonaromatic carbocyclic ring nor (b) a fused, 5-membered, nonaromatic heterocyclic ring having a sulfur atom as its sole heteroatom.

In another embodiment, a process of making the compound of formula I:

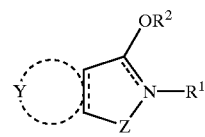

or a pharmaceutically acceptable salt, prodrug, metabolite, optical isomer or stereoisomer thereof, wherein $R^1$, $R^2$, n, y, m, A, Y, Z, $R^6$, $R^3$, $R^7$, and $R^8$ are as defined above, comprises the step of contacting an intermediate having formula II:

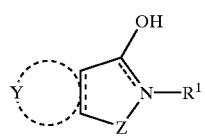

with $R_1X$ wherein X is a bromo, chloro or iodo moiety.

In yet another embodiment, the pharmaceutical composition of the invention comprises a pharmaceutically acceptable carrier and a compound of formula I:

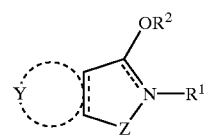

or a pharmaceutically acceptable salt, prodrug, metabolite, optical isomer or stereoisomer thereof, wherein:
  $R^1$, when present, is hydrogen or lower alkyl;
  $R^2$ is lower alkyl, aryl, aralkyl, lower alkanoyl, or —$(CH_2)_n$—$(CHOH)_y(CH_2)_m$A, wherein n is 1–4, y is 0 or 1, m is 0–5, and A is cycloalkyl, cycloalkenyl, lower alkanoyl, aryl, aralkyl, —NH$_2$, —NH-(lower alkyl),

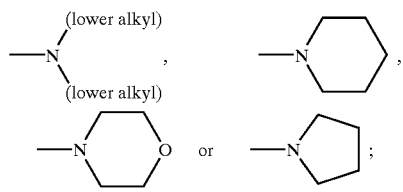

Y represents the atoms necessary to form a fused 5- to 6-membered ring that is aromatic or nonaromatic and carbocyclic or heterocyclic;

Z is
  (i) —CHR$^2$CHR$^3$— where R$^2$ and R$^3$ are independently hydrogen, alkyl, aryl or aralkyl;
  (ii) —R$^6$C=CR$^3$— where R$^6$ and R$^3$ are independently hydrogen, lower alkyl, aryl, aralkyl, chlorine, bromine or —NR$^7$R$^8$, where R$^7$ and R$^8$ are independently hydrogen or lower alkyl, or, R$^6$ and R$^3$, taken together, form a fused 5- to 6-membered ring that is aromatic or nonaromatic and carbocyclic or heterocyclic;
  (iii) —R$^2$C=N—;
  (iv) —CR$^2$(OH)—NR$^7$—; or
  (v) —C(O)—NR$^7$—;
provided that:
  when R$^6$ and R$^3$ form a fused benzene ring, then Y is neither (a) a fused, 6-membered, nonaromatic carbocyclic ring nor (b) a fused, 5-membered, nonaromatic heterocyclic ring having a sulfur atom as its sole heteroatom.

In particularly preferred embodiments of the above composition, the amount of the compound of formula I is present in an amount effective for inhibiting PARP activity, for effecting a neuronal activity not mediated by NMDA toxicity, or for treating arthritis, diabetes, an inflammatory bowel disorder, a cardiovascular disorder, septic shock, or cancer.

In an additional embodiments, a method of inhibiting PARP activity comprises administering a compound of formula I, as described above for the pharmaceutical compositions of the invention. In preferred embodiments, the amount of the compound administered in the methods of the invention is sufficient for effecting neuronal activity not mediated by NMDA toxicity or for treating arthritis, diabetes, inflammatory bowel disorders, cardiovascular disorders, septic shock, or cancer.

DETAILED DESCRIPTION OF THE INVENTION

Figure 1:
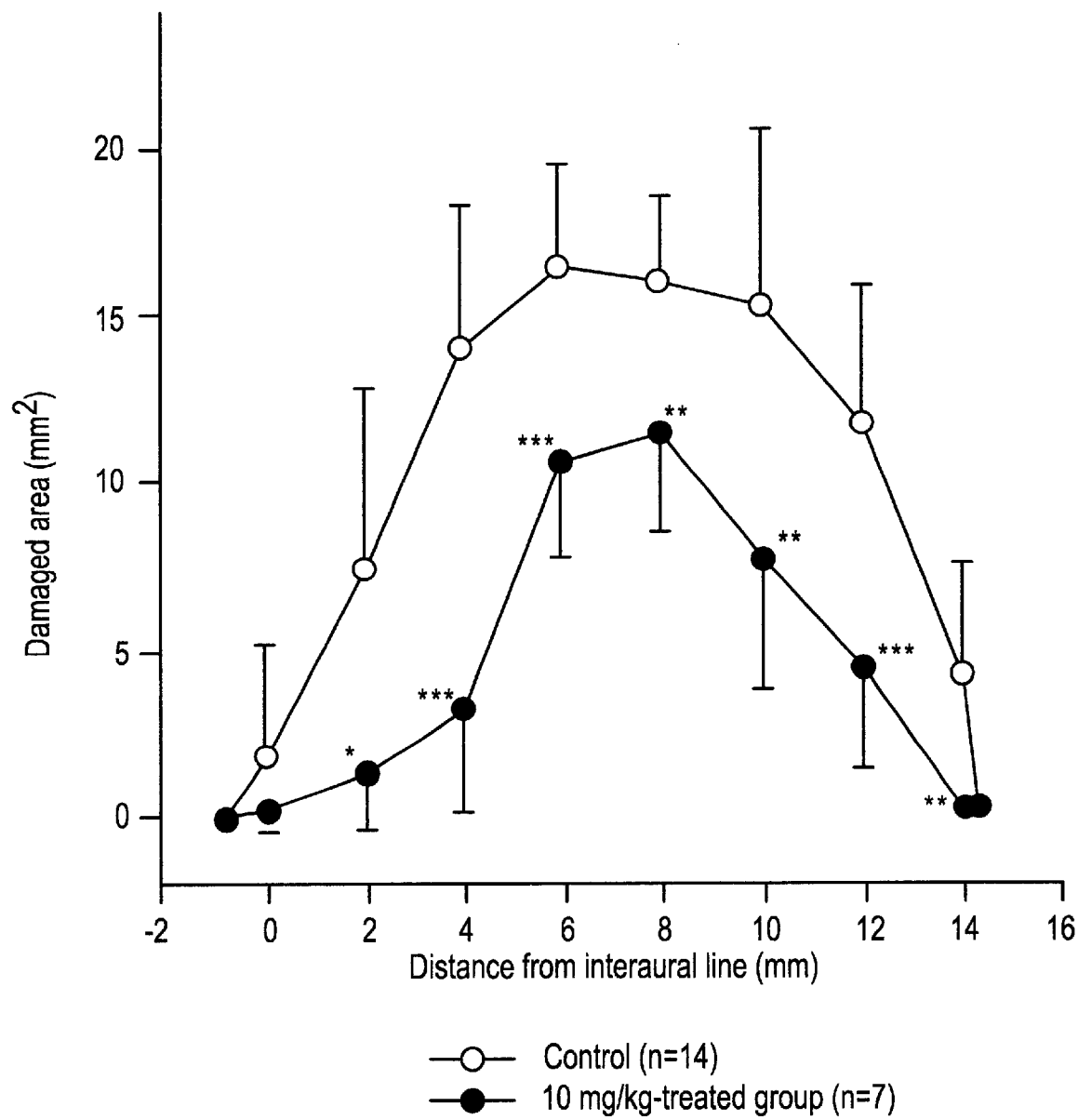
FIG. 1 shows the distribution of the cross-sectional infarct area at representative levels along the rostrocaudal axis, as measured from the interaural line in non-treated animals and in animals treated with 10 mg/kg of 3,4-dihydro-5-[4-(1-piperidinyl)-butoxyl]-1(2H)-isoquinolinone.

The alkoxy-substituted compounds of the present invention inhibit PARP activity. As such, they preferably also treat or prevent neural tissue damage resulting from cerebral ischemia and reperfusion injury or neurodegenerative diseases in a mammal. Preferably, the compounds of the invention effect a neuronal activity not mediated by NMDA toxicity. These compounds are thought to interfere with more than the glutamate neurotoxicity and NO-mediated biological pathways.

Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The term "isomers" refer to compounds having the same number and kind of atoms, and hence, the same molecular weight, but differing in respect to the arrangement or configuration of the atoms. "Stereoisomers" are isomers that differ only in the arrangement of atoms in space. "Enantiomers" are a pair of stereoisomers that are non-superimposable mirror images of each other.

"Diastereoisomers" are stereoisomers which are not mirror images of each other. "Racemic mixture" means a mixture containing equal, or roughly equal, parts of individual enantiomers. A "non-racemic mixture" is a mixture containing unequal, or substantially unequal, parts of individual enantiomers or stereoisomers.

The inventors have now discovered that select alkoxy-substituted compounds that inhibit PARP activity can ameliorate neural tissue damage, including that following focal ischemia and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO.

The compounds of the invention act as PARP inhibitors to treat or prevent neural tissue damage resulting from cerebral ischemia and reperfusion injury or neuro-degenerative diseases in a mammal. These compounds are thought to interfere with more than the NMDA-neurotoxicity and NO-mediated biological pathways. Preferably, the compounds of the invention exhibit an IC$_{50}$ for inhibiting PARP in vitro of about 100 µM or lower, more preferably, about 25 µM or lower.

The compound of the invention has the formula:

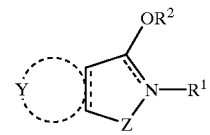

I or a pharmaceutically acceptable salt, prodrug, metabolite, optical isomer or stereoisomer thereof, wherein Y represents the atoms necessary to form a fused 5- to 6-membered ring that is aromatic or nonaromatic and carbocyclic or heterocyclic.

When Y forms a fused 5-membered carbocyclic ring, examples thereof include such rings as fused cyclopentane, cyclopentene, cyclopentadiene rings and the like. When Y forms a 5-membered N-containing heterocyclic ring, examples thereof include such rings as fused pyrrole, isopyrrole, imidazole, isoimidazole, pyrazole, pyrrolidine, pyrroline, imidazolidine, imidazoline, pyrazolidine, pyrazoline, isothiazole, isoxazole, furazan, furan, thiophene, 1,2,3-triazole, 1,2,4-triazole, dithiole, oxathiole, isoxazole, oxazole, thiazole, isothiazole, oxadiazole, oxatriazole, dioxazole, oxathiazole and the like rings.

When Y forms a fused 6-membered carbocyclic ring, examples of useful Y groups include a fused cyclohexane, cyclohexene, benzene or the like, optionally substituted with additional fused rings, thus forming, for example, naphthalene, anthracene, phenanthrene, benzonaphthene, and the like ring systems.

When Y forms a 6-membered N-containing heterocyclic ring, examples thereof include such rings as pyridine, pyrazine, pyrimidine, pyridazine, piperidine, piperazine, morpholine, pyran, pyrone, dioxin, triazine, oxazine, isoxazine, oxathiazine, oxadiazine, and the like rings.

Y may be aromatic, such as pyrrole, benzene or pyridine; or non-aromatic, such as cyclopentene, piperidyl or piperazinyl. Preferably, Y has at least one site of unsaturation.

Y may be unsubstituted or substituted with one or more non-interfering substituents. For example, Y may be substituted with an alkyl group such as methyl, ethyl, propyl, butyl, pentyl, hexyl, isopropyl, isobutyl, tertbutyl, n-pentyl, 2-methylpentyl, 2-methylhexyl, dodecyl, octadecyl and the like; with an alkenyl group such as ethenyl, propenyl, butenyl, pentenyl, 2-methylpentenyl, vinyl, isopropenyl, 2,2-dimethyl-1-propenyl, decenyl, hexadecenyl and the like; with an alkynyl group such as ethynyl, propynyl, butynyl, pentynyl, hexynyl, heptynyl, octynyl and the like; with an alkanoyl group such as formyl, acetyl, propanoyl, butanoyl, pentanoyl, benzoyl and the like; with a cycloalkyl group such as cyclobutyl, cyclopentyl, cyclohexyl, cycloheptyl, cyclooctanyl, cyclononyl, cyclodecyl and the like; with a cycloalkenyl group such as cyclopropenyl, cyclopentadienyl, cyclohexenyl, cyclooctenyl and the like; with an aralkyl group such as benzyl, 3-(1)-naphthyl-1-propyl, p-halobenzyl, p-ethylbenzyl, 1-phenyl-1-propyl, 3-pyridinyl-1-propyl, 1-phenyl-2-sec-butyl, 4-phenyl-4-methyl-1-pentyl and the like; or with an aryl group such as phenyl, naphthyl, pyridinyl, thienyl and the like.

"Aryl" is defined as an unsaturated carbocyclic or heterocyclic moiety which may be either unsubstituted or substituted with one or more non-interfering substituent(s). Examples include, without limitation, phenyl, naphthyl, indenyl, azulenyl, fluorenyl, anthracenyl, indolyl, isoindolyl, indolinyl, benzofuranyl, benzothiophenyl, indazolyl, benzimidazolyl, benzithiazolyl, tetrahydrofurnayl, tetrahydropyranyl, pyridyl, pyyrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbozolyl, acridinyl, phenazinyl, phenothiazinyl, phenoxazinyl and the like.

Possible substituents on an aryl group can be any non-interfering substituent. However, preferred substituents include, without limitation, alkyl, alkenyl, alkoxy, phenoxy, benzyloxy, cycloalkyl, cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, sulfhydryl, halo, haloalkyl, trifluoromethyl, aryl and aralkyl.

$R^1$, when present, is hydrogen or lower alkyl. Examples of useful alkyl groups are shown above as possible substitutents for Y.

$R^2$ is lower alkyl, aryl, aralkyl, lower alkanoyl, or —$(CH_2)_n(CHOH)_y(CH_2)_m$A wherein:
n is 1–4, preferably 1;
y is 0 or 1, preferably 0;
m is 0–5, preferably 0; and
A is cycloalkyl, cycloalkenyl, lower alkanoyl, aryl, aralkyl, —$NH_2$, —NH-(lower alkyl),

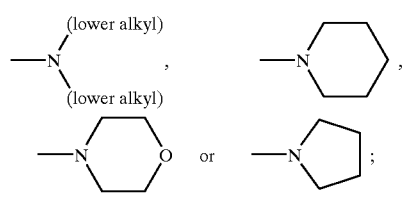

wherein "alkyl", "aryl" and "aralkyl" are as defined and/or exemplified above. Examples of useful alkanoyl groups include formyl, acetyl, propanoyl, sec-butanoyl, tert-pentanoyl (2,2-dimethylpropanoyl), benzoyl, hexanoyl, 3-methylpentanoyl, and the like.

When $R^2$ is —$(CH_2)_n(CHOH)_y(CH_2)_m$A, examples of useful groups include the following:

| n | y | m | A |
|---|---|---|---|
| 1 | 0 | 0 | cyclohexyl |
| 2 | 1 | 1 | cyclopentadienyl |
| 3 | 0 | 2 | propanoyl |
| 4 | 1 | 3 | phenyl |
| 1 | 0 | 4 | benzyl |
| 2 | 1 | 5 | —$NH_2$ |
| 3 | 0 | 1 | —N(CH$_3$)(CH$_2$CH$_3$) |
| 4 | 1 | 2 | —NHCH$_3$ |
| 1 | 0 | 3 | morpholinyl |
| 2 | 1 | 4 | piperidinyl |
| 3 | 0 | 5 | pyrrolidinyl |

Preferred $R^2$ groups include methyl, ethyl, propyl, butyl and benzyl groups, with benzyl being particularly preferred.

Z in formula I can be:
(i) —$CHR^2CHR^3$—;
(ii) —$R^6C=CR^3$—;
(iii) —$R^2C=N$—;
(iv) —$CR^2(OH)$—$NR^7$—; or
(v) —C(O)—$NR^7$—.
Preferably, however, Z is —$CHR^2CHR^3$—, —$R^6C=CR^3$— or —$R^2C=N$—.

$R^2$ and $R^3$ in formulas (i)–(v) above can be, independently, hydrogen; alkyl, such as methyl, ethyl, isopropyl, tert-butyl, n-pentyl, sec-octyl, dodecyl and the like; aryl; or aralkyl.

In formula (ii) (—R⁶C=CR³—), R⁶ and R³, independently can be hydrogen, alkyl as described above, phenyl, benzyl, chlorine, bromine, —NO₂, —COOH, —COOCH₃, or —NR⁷R⁸. When R₃ is —NR⁷R⁸, R⁸ is independently hydrogen or lower alkyl as described above.

Alternatively, R³ and R⁶, taken together, can form a fused aromatic or non-aromatic, mono-, bi- or tricyclic, carbocyclic or heterocyclic ring, wherein each individual ring has 5–6 ring member atoms. Examples of such rings include a fused cyclopentadiene, pyrrole, isopyrrole, imidazole, isoimidazole, triazole, pyrazole, pyridine, thiophene, furan, thiazole, isothiazole, oxazole, isoxazole, oxadiazole, benzene, naphthalene, acridine, cyclohexane, cyclohexene, indole, pyran, pyrone, pyridine, pyrazine, pyrimidine, pyridazine, or triazine nucleus. When Z is —R⁶C=CR³— and forms a fused aromatic or non-aromatic ring, the ring formed may be substituted with one or more non-hydrogen non-interfering substituents.

Possible substituents of Y, or of the fused ring formed when Z is —R⁶C=CR³—, include any substituent that does not interfere with the reactions and purposes of the invention. Examples include, without limitation, C₁–C₉ straight or branched chain alkyl, C₂–C₉ straight or branched chain alkenyl, C₁–C₉ alkoxy, C₂–C₉ alkenyloxy, phenoxy, benzyloxy, C₃–C₈ cycloalkyl, C₅–C₇ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, sulfhydryl, halo, haloalkyl, trifluoro-methyl, carbocyclic and heterocyclic moieties. Carbocylic moieties include alicyclic and aromatic structures.

Preferably, however, Z is —R⁶C=CR³— where R6 and R3, taken together, form a fused benzene ring, and neither Y nor Z is substituted with a non-hydrogen substituent.

In the compound of the invention, the multicyclic nuclear ring structure is preferably one of the following:

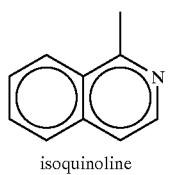
isoquinoline

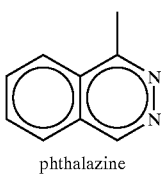
phthalazine

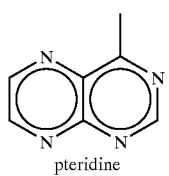
pteridine

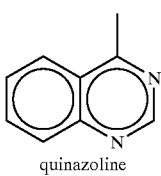
quinazoline

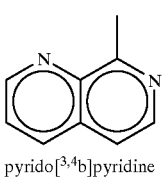
pyrido[3,4b]pyridine

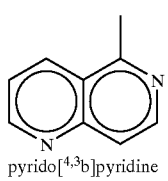
pyrido[4,3b]pyridine

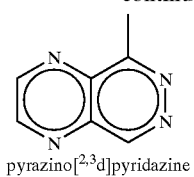
pyrazino[2,3d]pyridazine

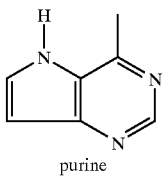
purine

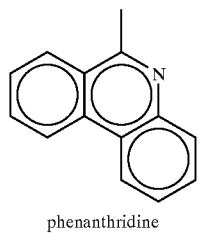
phenanthridine or pharmaceutically acceptable salt, prodrug, metabolite, optical isomer or stereoisomer thereof. Preferably the compound of the invention has an isoquinoline, a phenanthridine, a phthalazine, a pteridine, or a quinazoline nucleus. More preferably it has an isoquinoline or a phthalazine nucleus.

Preferred embodiments of the invention include 1-(benzyloxy)-5-methylphthalazine (I), 1-(methoxy)-5-methyl-phthalazine (II), 1-(ethoxy)-5-methylphthalazine (III), 1-(propoxy)-5-methylphthalazine (IV), 1-(butoxy)-5-methyl-phthalazine (V), 1-(methoxy)-5-hydroxyphthalazine (VI), 1-(ethoxy)-5-hydroxyphthalazine (VII), 1-(propoxyoxy)-5-hydroxy-phthalazine (VIII), 1-(butoxy)-5-hydroxyphthalazine (IX), 1-(benzyloxy)-5-methylisoquinoline (X), 1-(methoxy)-5-methyl-isoquinoline (XI), 1-(ethoxy)-5-methyl-isoquinoline (XII), 1-(propoxy)-5-methylisoquinoline (XIII), 1-(butoxy)-5-methylisoquinoline (XIV), 1-(ethoxy)-5-hydroxyisoquinoline (XV), 1-(propoxyoxy)-5-hydroxyisoquinoline (XVI) and 1-(butoxy)-5-hydroxy-isoquinoline (XVII), the structures of which follow.

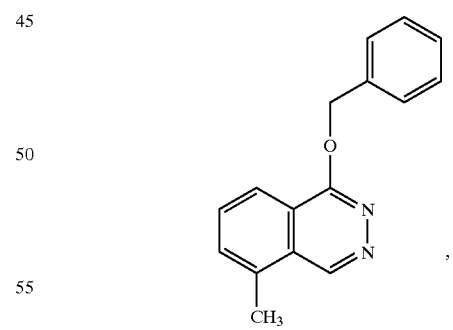

-continued
III
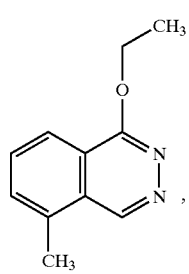
IV
V
VI
VII
-continued
VIII
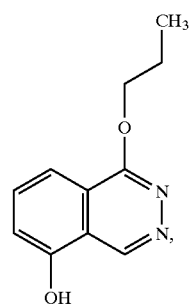
IX
X
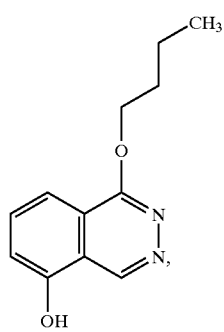
XI
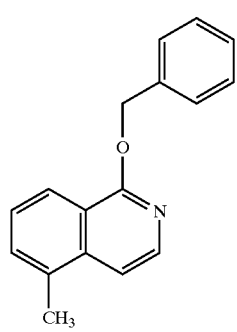
XII
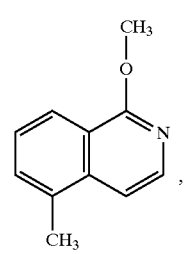

-continued

XIII

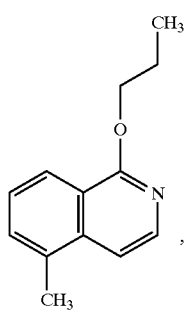

XIV

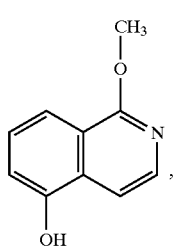

XV

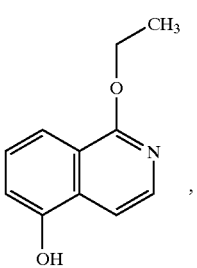

-continued

XVI

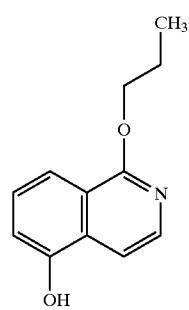

and

XVII

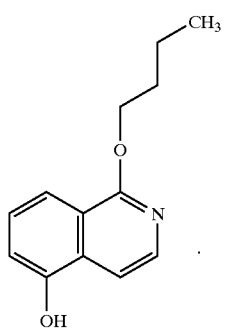

Most preferred embodiments include 1-(benzyloxy)-5-methyl-phthalazine (I) and 1-(benzyloxy)-5-methylisoquinoline (X), which are shown above.

Additional examples of useful inhibitors are shown below in Table I:

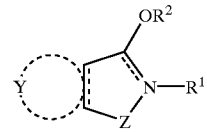

TABLE I

| R² | Y | Z |
|---|---|---|
| —CH₃ | cyclopentyl | —CH₂—CH₂— |
| —CH₂CH₃ | cyclopentenyl | —CH—CH₂—<br>     \|<br>    CH₃ |
| —CH₂CH₂CH₃ | furyl (O) | —CH—CH₂—<br>     \|<br>    C₆H₅ |
| —CH₂NHCH₂CH₃ | thienyl (S) | —CH—CH₂—<br>     \|<br>    CH₂—C₆H₅ |
| CH₂NHCH₂CH₂CH₂CH₃ | pyrazolyl (NH-N) | —CH—CH₂—<br>     \|<br>    CH<br>   /   \<br> CH₃   CH₃ |

TABLE I-continued

| R² | Y | Z |
|---|---|---|
| —CH₂—N(CH₃)₂ | imidazole (HN=CH-N=CH-CH) | $-CH-CH_2-$ with $C(CH_3)_3$ |
| —CH₂—N(CH₂CH₃)₂ | HN-CH=CH- (azetidine-like) | $-C=CH-$ with $C_2H_5$ |
| —CH₂—N(CH₂CH₂CH₃)₂ | N=N-NH (triazole) | $-C=CH-$ with $C_6H_5$ |
| —CH₂N(CH₂CH₂CH₂CH₃)₂ | N=CH-O (oxadiazole) | $-C=CH-$ with $CH_2-C_6H_5$ |
| —CH₂—NH₂ | cyclopentenyl | —CH₂—CH₂— |
| —CH₂—N(CH₃)₂ | cyclopentenyl | $-CH-CH_2-$ with $CH_3$ |
| —CH₂N(CH₂CH₃)₂ | furyl (O-CH=CH) | $-CH-CH_2-$ with $C_6H_5$ |
| CH₂CHOH—N(CH₃)₂ | thiazole (S-CH=N) | $-C=CH-$ with $Cl$ |
| CH₃-CHCHOH—N(CH₂CH₃)₂ | cyclohexadienyl | $-C=CH-$ with $Br$ |
| —CH₂—N—CH₂Ph | cyclohexyl | $-C=CH-$ with $NH-C_2H_5$ |
| -sec-C₆H₁₂N(CH₃)₂ | 2H-pyran | —CH₂=N— |
| -tert-C₆H₁₂N(CH₃)₂ | dihydropyran | $-C=N-$ with $CH(CH_3)(CH_3)$ |
| —CH₂—N(CH₂CH₃)₂ | pyridazine | $-CH-NH-$ with $OH$ |
| —C₂H₄—N(CH₂CH₃)₂ | pyridazine | $CH_3, CH_3$ on $-C-N-$ with $OH$ |

TABLE I-continued

| R² | Y | Z |
|---|---|---|
| —CH₂—(cyclohexyl) | N=CH—N=CH— (imidazole-like) | —CO—NH— |
| —(CH₂)₂(CHOH)CH₂—(cyclopentadienyl) | N=CH—CH=N— (pyrazine-like) | —CO—N(CH₃)(C₂H₅)— |
| —C(O)—CH₂CH₃ | piperazine | 3,4-dimethylthiophene |
| —(CH₂)₄(CHOH)(CH₂)₃Ph | N=N—CH=N—N=CH (tetrazine-like) | 2,3-dimethylphenyl |
| —(CH₂)₆—C₆H₅ | —N=CH—CH₂—O—CH₃ | 3,4-dimethylpyridine |
| —(CH₂)₄—N(morpholine) | —N(CH₃)—CH₂—CH₂—O—CH₃ | —CH₂—CH₂— |
| —(CH₂)₂CHOH(CH₂)₄—N(piperidine) | CH=C(CH₃)—CH=CH (isoprene-like) | —CH₂—CH₂— |
| —CH₂—(C₆H₅) | cyclopentane | —CH₂—CH₂— |
| —(CH₂)₂-cyclopentyl | cyclopentene | —CH(CH₃)—CH₂— |
| —CH₂—CHOH—CH₂—(cyclohexenyl) | furan | —CH(C₆H₅)—CH₂— |
| —(CH₂)₃CHOH—C(O)C₄H₉ | thiophene | —CH(CH₂—C₆H₅)—CH₂— |
| —(CH₂)₅-naphthyl | N=N—NH— (pyrazole-like) | —CH(CH(CH₃)₂)—CH₂— |

TABLE I-continued

| R² | Y | Z |
|---|---|---|
| —(CH₂)₆—[4-pyridyl] | [imidazole, N-H] | —CH—CH₂—, with CH₃, C(CH₃)₃ (i.e., —CH(−)—C(CH₃)₃ with a CH₂ branch) |
| —(CH₂)₂CHOH(CH₂)₂—C₆H₅ | [pyrrole, N-H] | —C=CH—, C₂H₅ |
| —(CH₂)₄—[morpholino] | [1,2,4-triazole, N-H] | —C=CH—, C₆H₅ |
| —(CH₂)₄—CHOH—(CH₂)₂—[piperidino] | [isoxazole-type, N—O] | —C=CH—, CH₂—C₆H₅ |
| —(CH₂)₄—[pyrrolidino] | [thiazole-type, N—S] | —C=CH—, Cl |
| -tert-C₅H₁₀N(CH₃)₂ | [cyclohexadiene] | —C=CH—, Br |
| —C₆H₁₂—N(CH₃)₂ | [cyclohexane] | —C=CH—, NH—C₂H₅ |
| -sec-C₆H₁₂N(CH₃)₂ | [2H-pyran] | —CH=N— |
| -tert-C₆H₁₂—N(CH₃)₂ | [3,4-dihydro-2H-pyran] | —C=N—, CH(CH₃)(CH₃) |
| —CH₂—N(CH₂CH₃)₂ | [pyridine] | —CH—NH—, OH |
| —C₂H₄—N(CH₂CH₃)₂ | [pyridazine] | CH₃ CH₃, —C—N—, OH |
| —C₃H₆—N(CH₂CH₃)₂ | [pyrimidine] | —CO—NH— |
| -sec-C₃H₆—N(CH₃)₂ | [pyrazine] | —CO—N—, C₂H₅ |

TABLE I-continued

| R² | Y | Z |
|---|---|---|
| —C₄H₈—N(CH₃)₂ | piperazine ring | 3,4-dimethylthiophene |
| -sec-C₄H₈—N(CH₃)₂ | N,N'-dimethylformamidine (N=N–CH, N–CH₃) | 2,3-dimethylphenyl |
| -tert-C₄H₈—N(CH₃)₂ | methoxymethylene-N-methylimine | 3,4-dimethylpyridine |
| —C₅H₁₀—N(CH₂CH₃)₂ | 2-methoxyethyl-N-methylamine | —CH₂—CH₂— |
| —CH₂—N(CH₂CH₃)₂ | 4-methyl-1,3-pentadiene | —CH₂—CH₂— |
| —C₃H₆—N(CH₂CH₃)₂ | 4-(3-piperidinyloxypropyl)-1,3-pentadiene | —CH₂—CH₂— |
| —CH₃ | cyclopentene | —CH₂—CH₂— |
| —CH₂(C₆H₅) | cyclopentene | —CH₂—CH₂— |
| —C(O)CH₃ | cyclopentene | —CH₂—CH₂— |
| —C₂H₅ | cyclopentadiene | —CH(CH₃)—CH₂— |
| —C₆H₅ | cyclopentadiene | —CH(CH₃)—CH₂— |
| —C(O)C₄H₉ | cyclopentadiene | —CH(CH₃)—CH₂— |
| —C₃H₇ | furan | —CH(C₆H₅)—CH₂— |

TABLE I-continued

| R² | Y | Z |
|---|---|---|
| 4-pyridyl | oxazoline (O-) | —CH(C₆H₅)—CH₂— |
| —C(O)CH₃ | oxazoline (O-) | —CH(C₆H₅)—CH₂— |
| C₆H₁₃ | thiazoline (S-) | —CH(CH₂—C₆H₅)—CH₂— |
| —CH₂(C₆H₅) | thiazoline (S-) | —CH(CH₂—C₆H₅)—CH₂— |
| —C(O)C₂H₅ | thiazoline (S-) | —CH(CH₂—C₆H₅)—CH₂— |
| —CH₃ | NH-pyrazoline | —CH(CH(CH₃)₂)—CH₂— |
| —CH₂(C₆H₅) | NH-pyrazoline | —CH(CH(CH₃)₂)—CH₂— |
| —C(O)CH₃ | NH-pyrazoline | —CH(CH(CH₃)₂)—CH₂— |
| —CH₂(C₆H₅) | NH-triazoline | —C(C₆H₅)=CH— |
| —C(O)CH₃ | NH-triazoline | —C(C₆H₅)=CH— |
| —CH₃ | isoxazoline | —C(CH₂—C₆H₅)=CH— |
| —CH₂(C₆H₅) | isoxazoline | —C(CH₂—C₆H₅)=CH— |
| —C(O)CH₃ | isoxazoline | —C(CH₂—C₆H₅)=CH— |
| —CH₃ | isothiazoline | —C(Cl)=CH— |

TABLE I-continued
| R² | Y | Z |
|---|---|---|
| —CH₂(C₆H₅) |  | 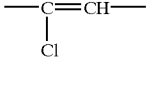 —C=CH— \| Cl |
|  O ‖ —CCH₃ | 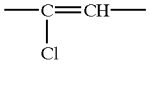 | —C=CH— \| Cl |
| —CH₃ |  | —C=CH— \| Br |
| —CH₂(C₆H₅) | 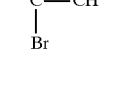 | —C=CH— \| Br |
|  O ‖ —CCH₃ | 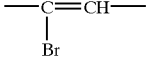 | —C=CH— \| Br |
| —CH₃ |  | —C=CH— \| NH—C₂H₅ |
| —CH₂(C₆H₅) | 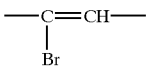 | —C=CH— \| NH—C₂H₅ |
| O ‖ —CC₂H₅ |  | —C=CH— \| NH—C₂H₅ |
| —CH₃ | 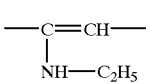 | —CH₂=N— |
| —CH₂(C₆H₅) |  | —CH₂=N— |
| O ‖ —CCH₃ | 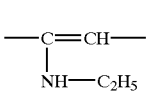 | —CH₂=N— |
| —CH₃ |  | —C=N— \| CH \| CH₃ CH₃ |
| —CH₂(C₆H₅) | 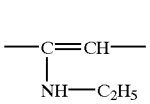 | —C=N— \| CH \| CH₃ CH₃ |

TABLE I-continued
| R² | Y | Z |
|---|---|---|
|  —CC₂H₅ (with =O) | 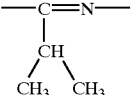 |  —C=N—CH(CH₃)(CH₃) |
| —CH₃ | 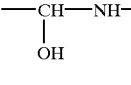 | —CH(OH)—NH— |
| —CH₂(C₆H₅) |  | —CH(OH)—NH— |
| —CCH₃ (with =O) | 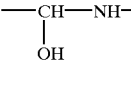 | —CH(OH)—NH— |
| —CH₃ |  | 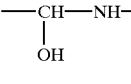 |
| —CH₂(C₆H₅) |  | 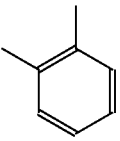 |
| —CC₂H₅ (with =O) |  | 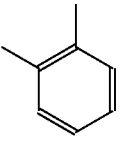 |
| —CH₃ |  | —CO—NH— |
| —CH₂(C₆H₅) | 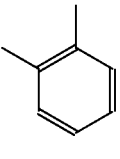 | —CO—NH— |
| —CCH₃ (with =O) |  | —CO—NH— |
| —CH₃ |  | —CO—N(C₂H₅)— |
| —CH₂(C₆H₅) |  | —CO—N(C₂H₅)— |

TABLE I-continued

| R² | Y | Z |
|---|---|---|
| —CC₂H₅ (C=O) | N=CH-N(CH₃)-CH=N(CH₃) | —CO—N(CH₃)(C₂H₅) |
| —CH₃ | piperazine (N,N'-dimethyl) | 3,4-dimethylthiophene |
| —CH₂(C₆H₅) | piperazine (N,N'-dimethyl) | 3,4-dimethylthiophene |
| —CCH₃ (C=O) | piperazine (N,N'-dimethyl) | 3,4-dimethylthiophene |
| —CH₃ | N=N-N(CH₃)-CH=N(CH₃) | 1,2-dimethylbenzene |
| —CH₂(C₆H₅) | N=N-N(CH₃)-CH=N(CH₃) | 1,2-dimethylbenzene |
| —CC₂H₅ (C=O) | N=N-N(CH₃)-CH=N(CH₃) | 1,2-dimethylbenzene |
| —CH₃ | morpholine-type (O-CH₂-N=CH-) | 3,4-dimethylpyridine |
| —CH₂(C₆H₅) | morpholine-type (O-CH₂-N=CH-) | 3,4-dimethylpyridine |
| —CCH₃ (C=O) | morpholine-type (O-CH₂-N=CH-) | 3,4-dimethylpyridine |

TABLE I-continued
| R² | Y | Z |
|---|---|---|
| —CH₃ | 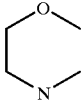 | —CH₂—CH₂— |
| —CH₂(C₆H₅) | 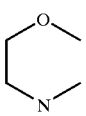 | —CH₂—CH₂— |
| 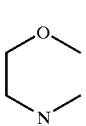 —CC₂H₅ (C=O) |  | —CH₂—CH₂— |
| —C₂H₅ |  | 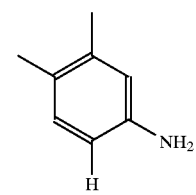 —C=CH— / CH₂—C₆H₅ |
| —CH₃ |  | 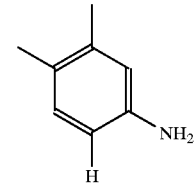 |
| —CH₂(C₆H₅) |  | 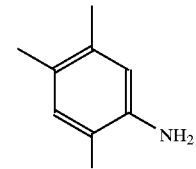 |
|  —CCH₃ (C=O) | 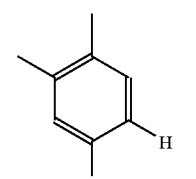 |  |
| —CH₃ | 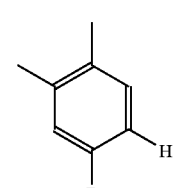 | |
| —CH₂(C₆H₅) | | |

TABLE I-continued

| $R^2$ | Y | Z |
|---|---|---|
| —C(O)C$_2$H$_5$ | phenyl | 4-methyl-bromophenyl |
| —CH$_3$ | 2-nitrophenyl | 4-methyl-aminophenyl |
| —CH$_2$(C$_6$H$_5$) | 2-nitrophenyl | 4-methyl-aminophenyl |
| —C(O)CH$_3$ | 2-nitrophenyl | 4-methyl-aminophenyl |
| —CH$_3$ | 2-thienyl | 4-methyl-bromophenyl |
| —CH$_2$(C$_6$H$_5$) | 2-thienyl | 4-methyl-bromophenyl |
| —C(O)C$_2$H$_5$ | 2-thienyl | 4-methyl-bromophenyl |

Also included are the pharmaceutically acceptable base or acid addition salts, prodrugs, metabolites, optical isomers and stereoisomers thereof.

The compounds of the invention may be useful in a free base form, in the form of pharmaceutically acceptable salts, pharmaceutically acceptable prodrugs, pharmaceutically acceptable metabolites, and in the form of pharmaceutically acceptable optical isomers or stereoisomers. These forms are all within the scope of the invention. In practice, the use of these forms amounts to use of the neutral compound.

"Pharmaceutically acceptable salt" refers to a salt of the inventive compounds which possesses the desired pharmacological activity and which is neither biologically nor otherwise undesirable. Organic acids can be used to produce salts such as acetate, adipate, alginate, aspartate, benzoate, benzenesulfonate, p-toluenesulfonate, bisulfate, sulfamate, butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts such as hydrochloride, hydrobromide, hydroiodide, and thiocyanate.

Examples of suitable base salts include hydroxides, carbonates, and bicarbonates of ammonia, alkali metal salts such as sodium, lithium and potassium salts, alkaline earth metal salts such as calcium and magnesium salts, aluminum salts, and zinc salts.

Salts may also be formed with organic bases. Organic bases suitable for the formation of pharmaceutically acceptable base addition salts of the compounds of the present invention include those that are non-toxic and strong enough to form such salts. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methylglucosamine; N-methyl-glucamine; L-glutamine; N-methylpiperazine; morpholine; ethylenediamine; N-benzylphenethylamine; (trihydroxy-methyl)aminoethane; and the like. See, for example, "Pharmaceutical Salts," J. Pharm. Sci., 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts of the basic compounds may be prepared either by dissolving the free base of a PARP inhibitor in an aqueous or an aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell.

Since must drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I (or functionalization) reactions generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE II

| | Phase I Reactions (functionalization reactions): |
|---|---|
| (1) | Oxidation via the hepatic microsomal P450 system: |
| | Aliphatic oxidation |
| | Aromatic hydroxylation |
| | N-Dealkylation |
| | O-Dealkylation |
| | S-Dealkylation |
| | Epoxidation |
| | Oxidative deamination |
| | Sulfoxide formation |
| | Desulfuration |
| | N-Oxidation and N-hydroxylation |
| | Dehalogenation |
| (2) | Oxidation via nonmicrosomal mechanisms: |
| | Alcohol and aldehyde oxidation |
| | Purine oxidation |
| | Oxidative deamination (monoamine oxidase and diamine oxidase) |
| (3) | Reduction: |
| | Azo and nitro reduction |
| (4) | Hydrolysis: |
| | Ester and amide hydrolysis |
| | Peptide bond hydrolysis |
| | Epoxide hydration |
| | Phase II Reactions (conjugation reactions): |
| (1) | Glucuronidation |
| (2) | Acetylation |
| (3) | Mercapturic acid formation |
| (4) | Sulfate conjugation |

TABLE II-continued

| | |
|---|---|
| (5) | N-, O-, and S-methylation |
| (6) | Trans-sulfuration |

The compounds of the present invention possess one or more asymmetric center(s) and thus can be produced as mixtures (racemic and non-racemic) of sereoisomers, or as individual R- and S-stereoisomers. The individual stereoisomers may be obtained by using an optically active starting material, by resolving a racemic or non-racemic mixture of an intermediate at some appropriate stage of synthesis, or by resolving a compound of formula Synthesis of Compounds Many nonalkoxy-substituted PARP inhibitors can be synthesized by known methods from starting materials that are known, are themselves commercially available, or may be prepared by standard techniques of organic chemistry used to prepare corresponding compounds in the literature. See, for example, Suto et al., "Dihydroisoquinolinones: The Design and Synthesis of a New Series of Potent Inhibitors of Poly(ADP-ribose) Polymerase", *Anticancer Drug Des.*, 6:107–17 (1991), which discloses processes for synthesizing a number of different PARP inhibitors.

For example, the alkoxy-substituted compounds of the invention may be prepared by reacting an alkoxide with a primary alkyl halide to yield an ether by an $S_N2$ pathway, a process known as the Williamson ether synthesis. Specifically, an intermediate having formula II:

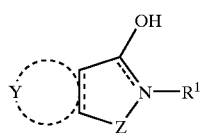

is reacted with $R^2X$, wherein X is bromo, chloro or iodo, as shown below:

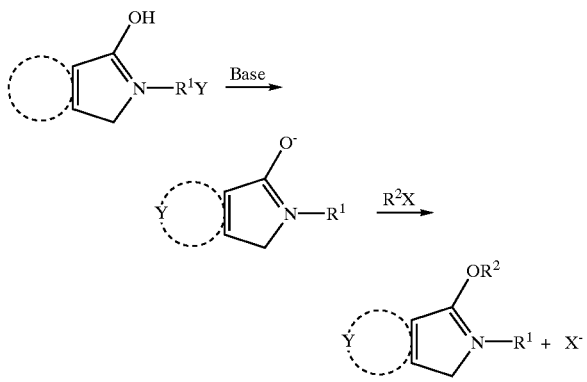

The alkoxide anion needed for the Williamson reaction to proceed is typically generated by reacting the compound of formula II with a strong base, such as sodium hydride, NaOH, KOH, $K_2CO_3$, $Na_2CO_3$, n-butyllithium or the like. The resulting acid-base reaction produces the intermediate anion for reaction with the halide $R^2X$.

More specific examples of this reaction include:

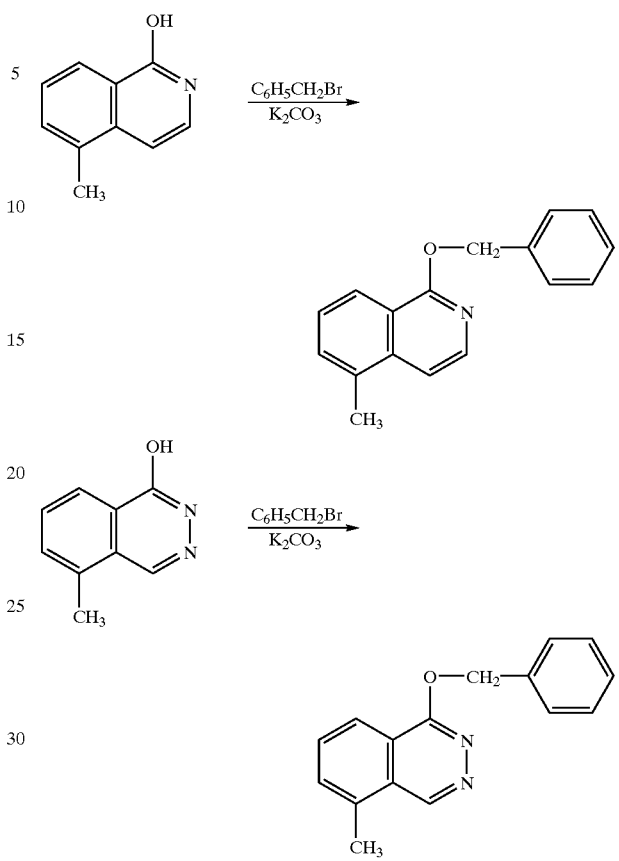

Typically, the reaction shown above takes place in a solvent that is inert with respect to both the intermediate of formula II or $R^2X$, and allows at least some of the $R^2X$ to go into solution. Typical solvents include, for example, methylene chloride, chloroform, tetrahydrofuran, dimethylformamide, and a variety of other inert organic solvents.

The above-described reaction can take place at varying temperatures depending, for example, upon the solvent used, the solubility of the intermediate of formula II and $R^2X$ in the solvent being used, and the susceptibility of the reactions to oxidize or participate in side reactions. Preferably, however, when the above reaction is used, it takes place at a temperature from about 0° C. to about 100° C., preferably at about room temperature.

The time required for the above reaction also can vary widely, depending on much the same factors. Typically, however, the reaction takes place within a time of about 5 minutes to about 24 hours, preferably from about 10 minutes to about two hours.

The addition sequence of the intermediate of formula III, the base, a solvent (if used), and the $R^2X$ compound, can vary significantly depending upon the relative reactivities of these materials, the purity of these materials, the temperature at which the reaction is performed, the degree of agitation used in the reaction, and the like. Preferably, however, the intermediate of formula II is first dissolved in a solvent, the base is first added, and the $R^2X$ compound is then added.

The product, a compound of formula I, is isolated from the reaction mixture by conventional techniques, such as by precipitating out, extraction with an immiscible solvent under appropriate pH conditions, evaporation, filtration, crystallization, or by column chromatography on silica gel and the like. Typically, however, the product is removed by either crystallization or column chromatography on silica gel.

Precursor compounds can be prepared by methods known in the art. An intermediate of formula II may be prepared by contacting an intermediate having formula III:

III with the hydroxide of a Group I element, such as KOH or NaOH, to initiate a fusion reaction, for example, KOH fusion. The intermediate of formula III can also be prepared by other methods known in the art. See L. Paquette, *Principles of Modern Heterocyclic Chemistry*, 273–307 (1968). Other variations and modifications of this invention using the synthetic pathways described above will be obvious to those skilled in the art.

Typically, the compounds of formula I used in the composition of the invention will have an $IC_{50}$ for inhibiting poly(ADP-ribose) polymerase in vitro of 100 $\mu$M or lower, preferably 25 $\mu$M or lower, more preferably 12 $\mu$M or lower and, even more preferably, 12 mM or lower.

Pharmaceutical Compositions

A further aspect of the present invention is directed to a pharmaceutical composition comprising a pharmaceutically acceptable carrier or a diluent and a therapeutically effective amount of a compound of formula I or a pharmaceutically acceptable salt, prodrug, metabolite, optical isomer or stereoisomer (hereafter, "a compound of formula I").

The formula I compounds of the invention are useful in the manufacture of pharmaceutical formulations comprising an effective amount thereof in conjunction with or as an admixture with excipients or carriers suitable for either enteral or parenteral application. As such, formulations of the present invention suitable for oral administration may be in the form of discrete units such as capsules, cachets, tablets, troche or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The composition will usually be formulated into a unit dosage form, such as a tablet, capsule, aqueous suspension or solution. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, corn starch and the like.

Particularly preferred formulations include tablets and gelatin capsules comprising the active ingredient together with (a) diluents, such as lactose, dextrose, sucrose, mannitol, sorbitol, cellulose, dried corn starch, and glycine; and/or (b) lubricants, such as silica, talcum, stearic acid, its magnesium or calcium salt, and polyethylene glycol.

Tablets may also contain binders, such as magnesium aluminum silicate, starch paste, gelatin, tragacanth, methylcellulose, sodium carboxymethylcellulose and polyvinylpyrrolidone; disintegrants, such as starches, agar, alginic acid or its sodium salt, and effervescent mixtures; and/or absorbents, colorants, flavors, and sweeteners. The compositions of the invention may be sterilized and/or contain adjuvants, such as preserving, stabilizing, swelling or emulsifying agents, solution promoters, salts for regulating osmotic pressure, and/or buffers. In addition, the composition may also contain other therapeutically valuable substances. Aqueous suspensions may contain emulsifying and suspending agents combined with the active ingredient. All oral dosage forms may further contain sweetening and/or flavoring and/or coloring agents.

These compositions are prepared according to conventional mixing, granulating, or coating methods, respectively, and contain about 0.1 to 75% of the active ingredient, preferably about 1 to 50% of the same. A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

When administered parenterally, the composition will normally be in a unit dosage, sterile injectable form (aqueous isotonic solution, suspension or emulsion) with a pharmaceutically acceptable carrier. Such carriers are preferably non-toxic, parenterally-acceptable and contain non-therapeutic diluents or solvents. Examples of such carriers include water; aqueous solutions, such as saline (isotonic sodium chloride solution), Ringer's solution, dextrose solution, and Hanks' solution; and nonaqueous carriers, such as 1,3-butanediol, fixed oils (e.g., corn, cottonseed, peanut, sesame oil, and synthetic mono- or di-glyceride), ethyl oleate, and isopropyl myristate.

Oleaginous suspensions can be formulated according to techniques known in the art using suitable dispersing or wetting agents and suspending agents. Among the acceptable solvents or suspending mediums are sterile fixed oils. For this purpose, any bland fixed oil may be used. Fatty acids, such as oleic acid and its glyceride derivatives, including olive oil and castor oil, especially in their polyoxyethylated forms, are also useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound. Common excipients include cocoa butter, beeswax and polyethylene glycols or other fatty emulsions or suspensions.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

Formulations suitable for nasal or buccal administration, (such as self-propelling powder dispensing formulations), may comprise about 0.1% to about 5% w/w of the active ingredient or, for example, about 1% w/w of the same. In addition, some formulations can be compounded into a sublingual troche or lozenge.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

In a preferred embodiment, the carrier is a solid biodegradable polymer with appropriate time release characteristics. The composition of the invention may then be molded into a solid implant suitable for providing efficacious concentrations of the compounds of the invention over a prolonged period of time without the need for frequent re-dosing.

The composition of the invention is preferably administered as a capsule or tablet containing a single or divided dose of the compound, or as a sterile solution, suspension, or emulsion, for parenteral administration in a single or divided dose.

In another preferred embodiment, the compounds of the invention can be prepared in lyophilizeid form. In this case, 1 to 100 mg of a PARP inhibitor may be lyophilized in individual vials, together with a carrier and a buffer, such as mannitol and sodium phosphate. The composition may then be reconstituted in the vials with bacteriostatic water before administration.

The compounds of the invention are used in the composition in amounts that are therapeutically effective. While the effective amount of the PARP inhibitor will depend upon the particular compound being used, amounts of the these compounds varying from about 1% to about 65% have been easily incorporated into liquid or solid carrier delivery systems.

Compositions and Methods for Effecting Neuronal Activity

Preferably, according to the invention, an effective therapeutic amount of the compounds and compositions described above are administered to animals to effect a neuronal activity, preferably one that is not mediated by NMDA neurotoxicity. Such neuronal activity may consist of stimulation of damaged neurons, promotion of neuronal regeneration, prevention of neurodegeneration and treatment of a neurological disorder. Accordingly, the present invention further relates to a method of effecting a neuronal activity in an animal, comprising administering an effective amount of the compound of formula I to said animal. Further, the compounds of the invention inhibit PARP activity and, thus, are believed to be useful for treating neural tissue damage, particularly damage resulting from cerebral ischemia and reperfusion injury or neurodegenerative diseases in mammals.

The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

The term "ischemia" refers to localized tissue anemia due to obstruction of the inflow of arterial blood. Global ischemia occurs when blood flow to the entire brain ceases for a period of time. Global ischemia may result from cardiac arrest. Focal ischemia occurs when a portion of the brain is deprived of its normal blood supply. Focal ischemia may result from thromboembolytic occlusion of a cerebral vessel, traumatic head injury, edema or brain tumor. Even if transient, both global and focal ischemia can cause widespread neuronal damage. Although nerve tissue damage occurs over hours or even days following the onset of ischemia, some permanent nerve tissue damage may develop in the initial minutes following the cessation of blood flow to the brain. Much of this damage has been attributed to glutamate toxicity and to the secondary consequences of tissue reperfusion, such as the release of vasoactive products by damaged endothelium and the release of cytotoxic products, such as free radicals and leukotrines, by the damaged tissue. Ischemia can also occur in the heart in myocardial infarction and other cardiovascular disorders in which the coronary arteries have been obstructed as a result of atherosclerosis, thrombi, or spasm.

The term "neural tissue damage resulting from ischemia and reperfusion injury and neurodegenerative diseases" includes neurotoxicity, such as seen in ascular stroke and global and focal ischemia.

The term "neurodegenerative diseases" includes Alzheimer's disease, Parkinson's disease and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemmorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed as having a neurodegenerative disease or who are at risk of developing a neurodegenerative disease. The term also encompasses preventing further neurodegeneration in patients who are already suffering from or have symptoms of a neurodegenerative disease.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barre syndrome; Alzheimer's disease; Huntington's Disease and Parkinson's disease.

The method of the present invention is particularly useful for treating a neurological disorder selected from the group consisting of: peripheral neuropathy caused by physical injury or disease state; head trauma, such as traumatic brain injury; physical damage to the spinal cord; stroke associated with brain damage, such as vascular stroke associated with hypoxia and brain damage, focal cerebral ischemia, global cerebral ischemia, and cerebral reperfusion injury; demyelinating diseases, such as multiple sclerosis; and neurological disorders related to neurodegeneration, such as Alzheimer's Disease, Parkinson's Disease, Huntington's Disease and amyotrophic lateral sclerosis (ALS).

Treating Other PARP-Related Disorders

The compounds, compositions and methods of the invention can also be used to treat a cardiovascular disorder in an animal, by administering an effective amount of the compound of formula to the animal. As used herein, the term "cardiovascular disorders" refers to those disorders that can either cause ischemia or are caused by reperfusion of the heart. Examples include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to PARP activation.

For example, the methods of the invention are believed to be useful for treating cardiac tissue damage, particularly damage resulting from cardiac ischemia or caused by reperfusion injury in mammals. The methods of the invention are particularly useful for treating cardiovascular disorders selected from the group consisting of: coronary artery disease, such as atherosclerosis; angina pectoris; myocardial infarction; myocardial ischemia and cardiac arrest; cardiac bypass; and cardiogenic shock. The methods of the invention are particularly helpful in treating the acute forms of the above cardiovascular disorders.

Further, the methods of the invention can be used to treat arthritis; diabetes; septic shock, such as endotoxic shock; and inflammatory bowel disorders, such as colitis and Crohn's disease.

Further, the methods of the invention can be used to treat cancer. The term "cancer" is interpreted broadly. The compounds of the present invention can be "anti-cancer agents", which term also encompasses "anti-tumor cell growth agents" and "anti-neoplastic agents".

For example, the methods of the invention are useful for treating cancers such as ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, prostate cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

Administration

For medical use, the amount required of a compound of formula I to achieve a therapeutic effect will vary according to the particular compound administered, the route of administration, the mammal under treatment, and the particular disorder or disease concerned. A suitable systemic dose of a compound of formula I for a mammal suffering from, or likely to suffer from, any condition as described herein is typically in the range of about 0.1 to about 100 mg of base per kilogram of body weight, preferably from about 1 to about 10 mg/kg of mammal body weight. It is understood that the ordinarily skilled physician or veterinarian will readily be able to determine and prescribe the amount of the compound effective for the desired prophylactic or therapeutic treatment.

In so proceeding, the physician or veterinarian may employ an intravenous bolus followed by an intravenous infusion and repeated administrations, as considered appropriate. In the methods of the present invention, the compounds may be administered, for example, orally, parenterally, by inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

Parenteral includes, but is not limited to, the following examples of administration: intravenous, subcutaneous, intramuscular, intraspinal, intraosseous, intraperitoneal, intrathecal, intraventricular, intrasternal or intracranial injection and infusion techniques, such as by subdural pump. Invasive techniques are preferred, particularly direct administration to damaged neuronal tissue. While it is possible for the compound of formula I to be administered alone, it is preferable to provide it as a part of a pharmaceutical formulation.

To be effective therapeutically as central nervous system targets, the compounds used in the methods of the present invention should readily penetrate the blood-brain barrier when peripherally administered. Compounds which cannot penetrate the blood-brain barrier, however, can still be effectively administered by an intraventricular route.

The compounds used in the methods of the present invention may be administered by a single dose, multiple discrete doses or continuous infusion. Since the compounds are small, easily diffusible and relatively stable, they are well suited to continuous infusion. Pump means, particularly subcutaneous or subdural pump means, are preferred for continuous infusion.

For the methods of the present invention, any effective administration regimen regulating the timing and sequence of doses may be used. Doses of the compounds preferably include pharmaceutical dosage units comprising an efficacious quantity of active compound. By an efficacious quantity is meant a quantity sufficient to inhibit PARP activity and/or derive the desired beneficial effects therefrom through administration of one or more of the pharmaceutical dosage units. In a particularly preferred embodiment, the dose is sufficient to prevent or reduce the effects of vascular stroke or other neurodegenerative diseases.

An exemplary daily dosage unit for a vertebrate host comprises an amount of from about 0.001 mg/kg to about 50 mg/kg. Typically, dosage levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex, and diet of the patient; the time of administration; the rate of excretion; any combination of the compound with other drugs; the severity of the particular disease being treated; and the form and route of administration. Typically, in vitro dosage-effect results provide useful guidance on the proper doses for patient administration. Studies in animal models can also be helpful. The considerations for determining the proper dose levels are well-known in the art.

In methods of treating nervous insult (particularly acute ischemic stroke and global ischemia caused by drowning or head trauma), the compounds of the invention can be co-administered with one or more other therapeutic agents, preferably agents which can reduce the risk of stroke (such as aspirin) and, more preferably, agents which can reduce the risk of a second ischemic event (such as ticlopidine).

The compounds and compositions can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the invention are administered in combination with one or more other therapeutic agents, specific dose levels for those agents will depend upon considerations such as those identified above for compositions and methods of the invention in general.

For example, Table II below provides known median dosages for selected chemotherapeutic agents that may be administered in combination with the compounds of the invention to such diseases or various cancers.

TABLE II

| CHEMOTHERAPEUTIC AGENT | MEDIAN DOSAGE |
| --- | --- |
| Asparaginase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg to 2 gm |
| Cyclophosphamide (non-lyophilized) | 100 mg to 2 gm |
| Cytarabine (lyophilized powder) | 100 mg to 2 gm |
| Dacarbazine | 100–200 mg |
| Dactinomycin | 0.5 mg |
| Daunorubicin | 20 mg |
| Diethylstilbestrol | 250 mg |
| Doxorubicin | 10–150 mg |
| Etidronate | 300 mg |
| Etoposide | 100 mg |
| Floxuridine | 500 mg |
| Fludarabine Phosphate | 50 mg |
| Fluorouracil | 500 mg to 5 gm |
| Goserelin | 3.6 mg |
| Granisetron Hydrochloride | 1 mg |
| Idarubicin | 5–10 mg |
| Ifosfamide | 1–3 gm |
| Leucovorin Calcium | 50–350 mg |
| Leuprolide | 3.75–7.5 mg |
| Mechlorethamine | 10 mg |
| Medroxyprogesterone | 1 gm |
| Melphalan | 50 gm |
| Methotrexate | 20 mg to 1 gm |
| Mitomycin | 5–40 mg |
| Mitoxantrone | 20–30 mg |
| Ondansetron Hydrochloride | 40 mg |
| Paclitaxel | 30 mg |
| Pamidronate Disodium | 30–90 mg |
| Pegaspargase | 750 units |
| Plicamycin | 2,500 mcgm |
| Streptozocin | 1 gm |
| Thiotepa | 15 mg |
| Teniposide | 50 mg |
| Vinblastine | 10 mg |
| Vincristine | 1–5 mg |
| Aldesleukin | 22 million units |
| Epoetin Alfa | 2,000–10,000 units |
| Filgrastim | 300–480 mcgm |
| Immune Globulin | 500 mg to 10 gm |
| Interferon Alpha-2a | 3–36 million units |
| Interferon Alpha-2b | 3–50 million units |
| Levamisole | 50 mg |
| Octreotide | 1,000–5,000 mcgm |
| Sargramostim | 250–500 mcgm |

For the methods of the present invention, any administration regimen regulating the timing and sequence of delivery of the compound can be used and repeated as necessary to effect treatment. Such regimen may include pretreatment and/or co-administration with additional therapeutic agents.

To maximize protection of nervous tissue from nervous insult, the compounds of the invention should be administered to the affected cells as soon as possible. In situations where nervous insult is anticipated, the compounds are advantageously administered before the expected nervous insult. Such situations of increased likelihood of nervous insult include surgery, such as carotid endarterectomy, cardiac, vascular, aortic, orthopedic surgery; endovascular procedures, such as arterial catheterization (carotid, vertebral, aortic, cardia, renal, spinal, Adamkiewicz); injections of embolic agents; the use of coils or balloons for hemostasis; interruptions of vascularity for treatment of brain lesions; and predisposing medical conditions such as crescendo transient ischemic attacks, emboli and sequential strokes.

Where pre-treatment for stroke or ischemia is impossible or impracticable, it is important to bring the compounds of the invention into contact with the affected cells as soon as possible, either during or after the event. In the time period between strokes, however, diagnosis and treatment procedures should be minimized to save the cells from further damage and death. Therefore, a particularly advantageous mode of administration with a patient diagnosed with acute multiple vascular strokes is by implantation of a subdural pump to deliver the compound(s) of the invention directly to the infarct area of the brain. Even if comatose, it is expected that the patient would recover more quickly that he or she would without this treatment. Moreover, in any conscious state of the patient, it is expected that any residual neurological symptoms, as well as the re-occurrence of stroke, would be reduced.

As to patients diagnosed with other acute disorders believed to be related to PARP activity, such as diabetes, arthritis and Crohn's disease, the compound of the invention should also be administered as soon as possible in a single or divided dose.

Depending on the patient's presenting symptoms and the degree of response to the initial administration of the compound of the invention, the patient may further receive additional doses of the same or different compounds of the invention, by one of the following routes: parenterally, such as by injection or by intravenous administration; orally, such as by capsule or tablet; by implantation of a biocompatible, biodegradable polymeric matrix delivery system comprising the compound; or by direct administration to the infarct area by insertion of a subdural pump or a central line. It is expected that the treatment would alleviate the disorder, either in part or in its entirety and that fewer further occurrences of the disorder would develop. It also is expected that the patient would suffer fewer residual symptoms.

Where a patient is diagnosed with an acute disorder prior to the availability of the compounds of the invention, the patient's condition may deteriorate due to the acute disorder and become a chronic disorder by the time that the compounds are available. Even when a patient receives a compound of formula I for the chronic disorder, it is also expected that the patient's condition would stabilize and actually improve as a result of receiving the compound.

EXAMPLES

The following examples are illustrative of preferred embodiments of the invention or related inventions and are not to be construed as limiting the present invention thereto. All polymer molecular weights are mean average molecular weights. All percentages are based on the percent by weight of the final delivery system or formulation prepared unless otherwise indicated, and all totals equal 100% by weight.

Example 1

Approximate $IC_{50}$ Data for Selected Compounds

The $IC_{50}$ of with respect to PARP inhibition was determined for several compounds by a PARP assay using purified recombinant human PARP from Trevigen (Gaithersburg, Md.), as follows: The PARP enzyme assay was set up on ice in a volume of 100 microliters consisting of 10 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction was initiated by incubating the mixture at 25° C. After 15 minutes' incubation, the reaction was terminated by adding 500 microliters of ice cold 20% (w/v) trichloroacetic acid. The precipitate formed was transferred onto a glass fiber filter (Packard Unifilter-GF/B) and washed three times with ethanol. After the filter was dried, the radioactivity was determined by scintillation counting.

Using the PARP assay described above, approximate $IC_{50}$ values were obtained for the following compounds:

| PARP Inhibitor | Approximate $IC_{50}$'s |
|---|---|
| 8-carbamoyl-naphthalene-1-carboxylic acid | .25 µM |
| 4-nitro-2H-isoquinolin-1-one | 5 µM |
| 3-phenyl-2H-isoquinolin-1-one | 30 µM |
| 1-oxo-1,2-dihydro-isoquinoline-4-carboxylic acid | 10 µM |
| 5-nitro-2H-isoquinolin-1-one | 10 µM |
| thieno[2,3-c]pyridin-7(6H)-one | 50 µM |

| PARP Inhibitor | Approximate IC$_{50}$'s |
|---|---|
| isoquinolinone with COOCH$_3$ substituent | 0.8 μM |
| phenanthridinone with NH$_2$ substituent | 4 μM |
| benzo-fused phenanthridinone | 100 μM |
| phenanthridinone with NO$_2$ substituent | 0.9 μM |
| unsubstituted phenanthridinone | 5.2 μM |
| phenanthridinone with Cl substituent | 0.7 μM |
| phenanthridinone with Br substituent | 1.1 μM |

Similar IC$_{50}$ values are obtained for the alkoxy-substituted compounds of the invention.

Example 2

Neuroprotective Effect of DPQ on Focal Cerebral Ischemia in Rats

Focal cerebral ischemia was produced by cauterization of the right distal MCA (middle cerebral artery) with bilateral temporary common carotid artery occlusion in male Long-Evans rats for 90 minutes. All procedures performed on the animals were approved by the University Institutional Animal Care and Use Committee of the University of Pennsylvania. A total of 42 rats (weights: 230–340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the compound, 3,4-dihydro-5-[4-(1-piperidinyl)-butoxy]-1(2H)-isoquinolinone ("DPQ") were dissolved in dimethyl sulfoxide (DMSO) using a sonicator. A volume of 1.28 ml/kg of the resulting solution was injected intraperitoneally into fourteen rats.

The rats were then anesthetized with halothane (4% for induction and 0.8%–1.2% for the surgical procedure) in a mixture of 70% nitrous oxide and 30% oxygen. The body temperature was monitored by a rectal probe and maintained at 37.5±0.5° C. with a heating blanket regulated by a homeothermic blanket control unit (Harvard Apparatus Limited, Kent, U.K.). A catheter (PE-50) was placed into the tail artery, and arterial pressure was continuously monitored and recorded on a Grass polygraph recorder (Model 7D, Grass Instruments, Quincy, Mass.). Samples for blood gas analysis (arterial pH, PaO$_2$ and PaCO$_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA, 4 mm lateral to the sagittal suture and 5 mm caudal to the coronal suture. The dura mater and a thin inner bone layer were kept, care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral ischemia was produced by cauterization of the distal portion of the right MCA with bilateral temporary common carotid artery (CCA) occlusion by the procedure of Chen et al., "A Model of Focal Ischemic Stroke in the Rat: Reproducible Extensive Cortical Infarction", *Stroke* 17:738–43 (1986) and/or Liu et al., "Polyethylene Glycol-conjugated Superoxide Dismutase and Catalase Reduce Ischemic Brain Injury", *Am. J. Physiol.* 256:H589–93 (1989), both of which are hereby incorporated by reference.

Specifically, bilateral CCA's were isolated, and loops made from polyethylene (PE-10) catheter were carefully passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentamicin sulfate (10 mg/ml) was topically applied to the wounds to prevent infection. The anesthetic was discontinued, and the animal was returned to his cage after awakening. Water and food were allowed ad libitum. Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM-4000C, ASI Instruments, Warren, Mich.). The brain slices were incubated in phosphate-buffered saline containing 2% 2,3,5-triphenyltetrazolium chloride (TTC) at 37° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume", *J. Cereb. Blood Flow Metabol.* 10:290–93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group, as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-[4-(1-piperidinyl)-butoxy]-1(2H)-isoquinolinone. The area of damage was expressed as mean±standard deviation. Significant differences between the 10 mg-treated group and the control group were indicated (*p<0.02, p<0.01, p<0.001). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group (106.7±23.2 mm$^3$, p<0.001), the 10 mg/kg-treated group (76.4±16.8 mm$^3$, p<0.001), and the 20 mg/kg-treated group (110.2±42.0 mm$^3$, p<0.01), compared to the control group (165.2±34.0 mm$^3$. The data are expressed as mean±standard deviation. The significance of differences between groups was determined using an analysis of variance (ANOVA) followed by Student's t-test for individual comparisons.

There was no significant difference between the control and the 40 mg/kg-treated group (135.6±44.8 mm$^3$). However, there were significant differences between the 5 mg/kg-treated group and the 10 mg/kg-treated group (p<0.02), and between the 10 mg/kg-treated group and the 40 mg/kg-treated group (p<0.01), as shown in FIG. 2.

Figure 2:
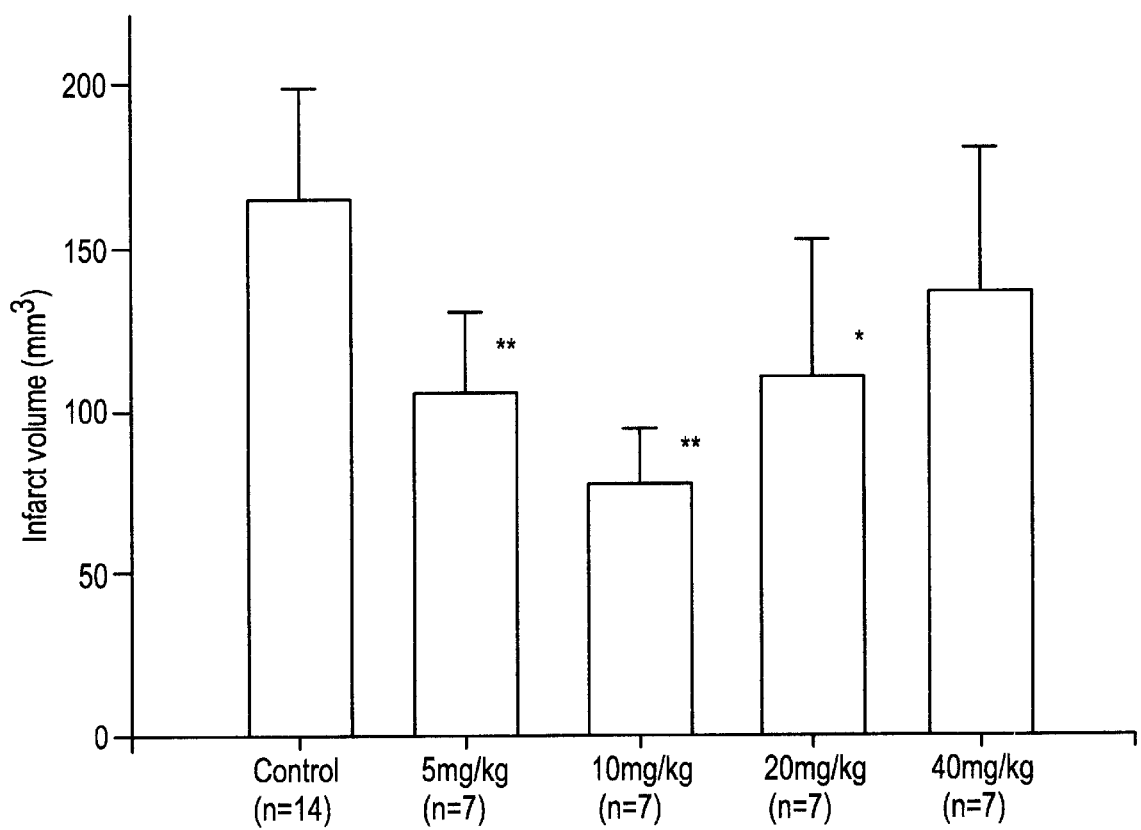
FIG. 2 shows the effect of intraperitoneal administration of 3,4-dihydro-5-[4-(1-piperidinyl)butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoquinolinone on the infarct volume was depicted graphically. The volumes of infarct were expressed as mean±standard deviation. Significant differences between the treated groups and the control group were indicated (*p<0.01, **p<0.001) . It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases ($PaO_2$, $PaCO_2$ and pH) were within the physiological range in the control and treated groups with no significant differences in these parameters among the five groups, as shown below in Table 2. A "steady state" MABP was taken following completion of the surgical preparation, just prior to occlusion; an "ischemia" MABP was taken as the average MABP during occlusion. See Table III below:

TABLE III

|  | $PaO_2$ (mm Hg) | $PaCO_2$ (mm Hg) | pH | MABP (mm Hg) Steady | Ischemia State |
|---|---|---|---|---|---|
| Control group (n = 4) | 125 ± 21 | 38.6 ± 4.6 | 7.33 ± 0.05 | 79 ± 14 | 91 ± 13** |
| 5 mg/kg-treated group (n = 7) | 126 ± 20 | 38.0 ± 2.8 | 7.36 ± 0.02 | 78 ± 5 | 91 ± 12** |

TABLE III-continued

|  | PaO$_2$ (mm Hg) | PaCO$_2$ (mm Hg) | pH | MABP (mm Hg) Steady | MABP (mm Hg) Ischemia State |
|---|---|---|---|---|---|
| 10 mg/kg-treated group (n = 7) | 125 ± 16 | 39.3 ± 5.2 | 7.34 ± 0.03 | 80 ± 9 | 90 ± 14* |
| 20 mg/kg-treated group (n = 7) | 122 ± 14 | 41.3 ± 2.8 | 7.35 ± 0.23 | 79 ± 10 | 91 ± 12** |
| 40 mg/kg-treated group (n = 7) | 137 ± 17 | 39.5 ± 4.7 | 7.33 ± 0.24 | 78 ± 4 | 88 ± 12* |

*= Significantly different from the steady state value, p < 0.05.
**= Significantly different from the steady state value, p < 0.01.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxynitrite, in addition to oxygen-derived free radicals. All of these radicals have been shown to cause DNA strand breaks and to activate PARP.

This example provided evidence that the related compounds of the present invention are effective in inhibiting PARP activity.

Example 3

Assay for Neuroprotective Effects on Focal Cerebral Ischemia in Rats

Focal cerebral ischemia experiments are performed using male Wistar rats weighing 250–300 g, which are anesthetized with 4% halothane. Anesthesia is maintained with 1.0–1.5% halothane until the end of surgery. The animals are installed in a warm environment to avoid a decrease in body temperature during surgery.

An anterior midline cervical incision is made. The right common carotid artery (CCA) is exposed and isolated from the vagus nerve. A silk suture is placed and tied around the CCA in proximity to the heart. The external carotid artery (ECA) is then exposed and ligated with a silk suture. A puncture is made in the CCA and a small catheter (PE 10, Ulrich & Co., St-Gallen, Switzerland) is gently advanced to the lumen of the internal carotid artery (ICA). The pterygopalatine artery is not occluded. The catheter is tied in place with a silk suture. Then, a 4-0 nylon suture (Braun Medical, Crissier, Switzerland) is introduced into the catheter lumen and is pushed until the tip blocks the anterior cerebral artery. The length of catheter into the ICA is approximately 19 mm from the origin of the ECA. The suture is maintained in this position by occlusion of the catheter with heat. One cm of catheter and nylon suture are left protruding so that the suture can be withdrawn to allow reperfusion. The skin incision is then closed with wound clips.

The animals are maintained in a warm environment during recovery from anesthesia. Two hours later, the animals are re-anesthetized, the clips are discarded, and the wound is re-opened. The catheter is cut, and the suture is pulled out. The catheter is then obturated again by heat, and wound clips are placed on the wound. The animals are allowed to survive for 24 hours with free access to food and water. The rats are then sacrificed with $CO_2$ and decapitated.

The brains are immediately removed, frozen on dry ice and stored at −80° C. The brains are then cut in 0.02 mm-thick sections in a cryocut at −19° C., selecting one of every 20 sections for further examination. The selected sections are stained with cresyl violet according to the Nissl procedure. Each stained section is examined under a light microscope, and the regional infarct area is determined according to the presence of cells with morphological changes.

Various doses of the compounds of the invention are tested in this model. The compounds are administered in either a single dose or a series of multiple doses, i.p. or i.v., at different times, both before or after the onset of ischemia. Compounds of the invention are found to provide protection from ischemia in the range of about 20 to 80%.

Example 4

Effects on Heart Ischemia/Reperfusion Injury in Rats

Female Sprague-Dawley rats, each weighing about 300–350 g are anesthetized with intraperitoneal ketamine at a dose of 150 mg/kg. The rats are endotracheally intubated and ventilated with oxygen-enriched room air using a Harvard rodent ventilator. Polyethylene catheters inserted into the carotid artery and the femoral vein are used for artery blood pressure monitoring and fluid administration respectively. Arterial $pCO_2$ is maintained between 35 and 45 mm Hg by adjusting the respirator rate. The rat chests are opened by median sternotomy, the pericardium is incised, and the hearts are cradled with a latex membrane tent. Hemodynamic data are obtained at baseline after at least a 15-minute stabilization period following the end of the surgical operation. The LAD (left anterior descending) coronary artery is ligated for 40 minutes, and then reperfused for 120 minutes. After 120 minutes' reperfusion, the LAD artery is re-occluded, and a 0.1 ml bolus of monastral blue dye is injected into the left atrium to determine the ischemic risk region.

The hearts are then arrested with potassium chloride and cut into five 2–3 mm thick transverse slices. Each slice is weighed and incubated in a 1% solution of trimethyltetrazolium chloride to visualize the infarcted myocardium located within the risk region. Infarct size is calculated by summing the values for each left ventricular slice and is further expressed as a fraction of the risk region of the left ventricle.

Various doses of the compounds of the invention are tested in this model. The compounds are given either in a single dose or a series of multiple doses, i.p. or i.v., at different times, both before or after the onset of ischemia. The compounds of the invention are found to have ischemia/reperfusion injury protection in the range of 10 to 40 percent. Therefore, they protect against ischemia-induced degeneration of rat hippocampal neurons in vitro.

Example 5

Vascular Stroke Protection

A patient just diagnosed with acute vascular stroke is immediately administered parenterally, either by intermittent or continuous intravenous administration, a compound of formula I, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects post-stroke. In addition, it is expected that the re-occurrence of vascular stroke would be prevented or reduced.

Example 6

Treatment of Vascular Stroke

A patient has just been diagnosed with acute multiple vascular strokes and is comatose. Immediately, a physician or a nurse parenterally administers a compound of formula I, either as a single dose or as a series of divided doses. Due to the comatose state of the patient, the patient also receives the same or a different PARP inhibitor by intermittent or continuous administration via implantation of a biocompatible, biodegradable polymeric matrix delivery system comprising a compound of formula I, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of vascular stroke would be reduced.

Example 7

Preventing Cardiac Reperfusion Injury

A patient is diagnosed with life-threatening cardiomyopathy and requires a heart transplant. Until a donor heart is found, the patient is maintained on Extra Corporeal Oxygenation Monitoring (ECMO).

A donor heart is then located, and the patient undergoes a surgical transplant procedure, during which the patient is placed on a heart-lung pump. The patient receives a compound of the invention intracardiac within a specified period of time prior to re-routing his or her circulation from the heart-lung pump to his or her new heart, thus preventing cardiac reperfusion injury as the new heart begins to beat independently of the external heart-lung pump.

Example 8

Septic Shock Assay

Groups of 10 C57/BL male mice weighing 18 to 20 g were administered a test compound, 1-carboxynaphthalene-1-carboxamide at the doses of 60, 20, 6 and 2 mg/kg, daily, by intraperitoneal (IP) injection for three consecutive days. Each animal was first challenged with lipopolysaccharide (LPS, from *E. Coli,* $LD_{100}$ of 20 mg/animal IV) plus galactosamine (20 mg/animal IV). The first dose of test compound in a suitable vehicle was given 30 minutes after challenge, and the second and third doses were given 24 hours later on day 2 and day 3 respectively, with only the surviving animals receiving the second or third dose of the test compound. Mortality was recorded every 12 hours after challenge for the three-day testing period. 1-Carboxy-naphthalene-1-carboxamide provided a protection against mortality from septic shock of about 40%. Based on these results, other compounds of the invention are expected to provide a protection against mortality exceeding about 35%.

Example 9

Radiosensitization

Before undergoing radiation therapy to treat cancer, a patient may be administered an effective amount of a compound or a pharmaceutical composition of the present invention. It is expected that the compound or pharmaceutical composition would act as a radiosensitizer and make the tumor more susceptible to radiation therapy.

The invention being thus described, it will be obvious that the same may be varied in many ways. Such variations are not to be regarded as a departure from the spirit and scope of the invention, and all such modifications are intended to be included within the scope of the following claims.

We claim:
1. A compound of formula I:

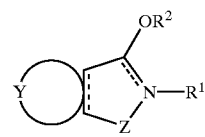

or a pharmaceutically acceptable salt, hydrate, ester, solvate, prodrug, metabolite, stereoisomer, or mixtures thereof, wherein:

$R^1$, when present, is hydrogen or lower alkyl;

$R^2$ is lower alkyl, aryl, aralkyl, lower alkanoyl, or —$(CH_2)_n$—$(CHOH)_y(CH_2)_m$A, wherein n is 1–4, y is 0 or 1, m is 0–5, and A is cycloalkyl, cycloalkenyl, lower alkanoyl, aryl, aralkyl, —$NH_2$, —NH-(lower alkyl),

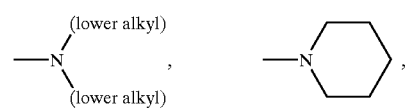

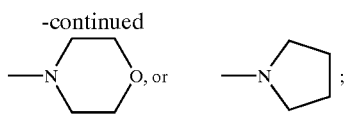

Y represents the atoms necessary to form a fused 5- to 6-membered substituted or unsubstituted ring that is aromatic or nonaromatic and carbocyclic or heterocyclic;

Z is
(i) —$CHR^2CHR^3$— where $R^2$ and $R^3$ are independently hydrogen, alkyl, aryl or aralkyl;
(ii) —$R^6C$=$CR^3$— where $R^6$ and $R^3$ are independently hydrogen, lower alkyl, aryl, aralkyl, chlorine, bromine or —$NR^7R^8$, where $R^7$ and $R^8$ are independently hydrogen or lower alkyl, or, $R^6$ and $R^3$, taken together, form a fused 5- to 6-membered ring that is aromatic or nonaromatic and carbocyclic or heterocyclic;
(iii) —$R^2C$=N—;
(iv) —$CR^2(OH)$—$NR^7$—; or
(v) —C(O)—$NR^7$—;

provided that:
when $R^6$ and $R^3$ form a fused benzene ring, then Y is neither (a) a fused, 6-membered, nonaromatic carbocyclic ring nor (b) a fused, 5-membered, nonaromatic heterocyclic ring having a sulfur atom as its sole heteroatom;
when Z is (i) or (ii), then Y is not a 6-membered, aromatic carbocyclic ring;
when Z is (iii), then $R^2$ is not lower alkyl, aryl or aralkyl.

2. The compound of claim 1, wherein Y has at least one site of unsaturation.

3. The compound of claim 1, wherein Z is (i) —$CHR^2CHR^3$—, (ii) —$R^6C$=$CR^3$—, or (iii) —$R^2C$=N—.

4. The compound of claim 1, wherein said compound has an isoquinoline, a phenanthridine, a phthalazine, a pteridine, or a quinazoline nucleus.

5. The compound of claim 4, wherein said compound has an isoquinoline or phthalazine nucleus.

6. The compound of claim 1, wherein Y represents the atoms necessary to form a 5- to 6-membered carbocyclic ring.

7. The compound of claim 6, wherein Y is aromatic.

8. The compound of claim 6, wherein Y represents the atoms necessary to form a fused benzene ring.

9. The compound of claim 6, wherein Y is nonaromatic.

10. The compound of claim 1, wherein Y represents the atoms necessary to form a 5- to 6-membered N-containing ring.

11. The compound of claim 10, wherein Y is aromatic.

12. The compound of claim 10, wherein Y is nonaromatic.

13. The compound of claim 1, wherein said compound has an $IC_{50}$ of 100 µM or lower for inhibiting poly(ADP-ribose) polymerase in vitro.

14. The compound of claim 1, wherein said compound has an $IC_{50}$ of 25 µM or lower for inhibiting poly(ADP-ribose) polymerase in vitro.

15. A compound of claim 1 wherein Y is substituted with at least one substituent selected from the group consisting of an alkyl, an alkenyl, an alkynyl and an alkanoyl.

16. The compound of claim 1 wherein Z is (iv) or (v).

* * * * *